(12) United States Patent
Royal et al.

(10) Patent No.: US 8,630,869 B2
(45) Date of Patent: Jan. 14, 2014

(54) DENTAL IMPLANT SYSTEM AND METHOD

(75) Inventors: Bret Royal, La Vernia, TX (US); Norman L. Jacobson, San Antonio, TX (US)

(73) Assignee: iMagDent Management and Development Services, L.L.C., San Antonio, TX (US)

( * ) Notice: Subject to any disclaimer, the term of this patent is extended or adjusted under 35 U.S.C. 154(b) by 34 days.

(21) Appl. No.: 13/103,235

(22) Filed: May 9, 2011

(65) Prior Publication Data

US 2012/0065985 A1 Mar. 15, 2012

Related U.S. Application Data

(60) Provisional application No. 61/332,489, filed on May 7, 2010.

(51) Int. Cl.
*G06Q 50/00* (2012.01)

(52) U.S. Cl.
USPC .............................................................. 705/2

(58) Field of Classification Search
USPC .................... 705/2; 606/4; 364/401; 433/215
See application file for complete search history.

(56) References Cited

U.S. PATENT DOCUMENTS

| | | | |
|---|---|---|---|
| 6,000,828 A * | 12/1999 | Leet | 705/2 |
| 6,772,026 B2 | 8/2004 | Bradbury et al. | |
| 7,383,198 B1 | 6/2008 | Sepe | |
| 2003/0018484 A1 | 1/2003 | Franks et al. | |
| 2004/0152036 A1 | 8/2004 | Abolfathi | |
| 2004/0197728 A1 | 10/2004 | Abolfathi et al. | |
| 2005/0182654 A1 | 8/2005 | Abolfathi et al. | |
| 2007/0161972 A1 * | 7/2007 | Felberg et al. | 606/4 |
| 2007/0226005 A1 | 9/2007 | Smith et al. | |
| 2008/0033754 A1 | 2/2008 | Smith et al. | |
| 2009/0298017 A1 | 12/2009 | Boerjes et al. | |
| 2010/0105011 A1 * | 4/2010 | Karkar et al. | 433/215 |

OTHER PUBLICATIONS

Roe Dental Laboratory website (www.roedentallab.com); (C) 2005.*
"Materialise Dental launches SimPlant® Crystal!" availabe at <http://www.materialise.com/materialise/view/en/2539986-Materialise+Dental+launches+>, Aug. 28, 2009. (p. 1).
"Collaborative software connects dental professionals on a global scale" available at <http://www.dental-tribune.com/articles/content/id/687/scope/news/region/usa>, Aug. 27, 2009. (pp. 1-2).

* cited by examiner

*Primary Examiner* — John Pauls
(74) *Attorney, Agent, or Firm* — Meyertons, Hood, Kivlin, Kowert & Goetzel, P.C.; Eric B. Meyertons

(57) ABSTRACT

A method includes receiving an input indicative of a user's geographic location and providing a listing of providers available for use in planning and implementing a dental implant treatment plan based on the user's geographic location. A listing of dental implant treatment and planning software options available for use in planning and implementing the dental implant ireatment plan for the patient are provided and selected by the user. Dental implant information for the patient is received from the user. A listing of user selectable dental implant treatment plan options is provided. A cost associated with the user selectable dental implant treatment plan options available for inclusion in the dental implant treatment plan are provided and the cost is updated based on the user's selection of the user selectable dental implant treatment plan options.

27 Claims, 12 Drawing Sheets

Welcome to Implant Concierge!

Implant Concierge, your personal virtual treatment plan coordinator, will guide you through a series of questions that will simplify your next CT guided surgery case.

Step One: Case Information

*621* Start a New Case
View Current Cases

*613a* → TOTAL COST: $1,110

Patient Name
First: Walter    Middle: N    Last: Johnson

Step Two: Case Plan
Answer the questions below and click the "Next" button. Based on your answers, Implant Concierge will begin to customize the case to your exact specifications.

Implant Planning Software
○ Procera Nobel Guide
● Simplant
○ Keystone EZ Guide
○ Facilitate
○ Navigate
○ I do not have a software preference.

Arch Selection
This case will involve:
○ maxilla    ○ mandible    ● both

Radiographic Prosthesis
● Design and order a radiographic prosthesis from Implant Concierge. - $1000 Max
○ I will furnish a radiographic prosthesis for the CBCT Scan.
○ This case will not require a radiographic prosthesis.

CT/CBCT X-Ray Location
I will refer the patient to an iMagDent location for a CBCT scan. - $200
○ Lafayette, Louisiana    ○ Dallas, Texas
○ Webster, New York      ○ Fort Worth, Texas
○ Memphis, Tennessee    ○ Houston, Texas          ←— *612a*
● Austin, Texas          ○ San Antonio, Texas
~OR~
I will acquire CBCT scan from another source. - $10
○ Medical CT             ○ My CBCT
○ CBCT Imaging Center    ○ Other dentist CBCT Radiology Interpretation
● Yes, I want a Board certified Oral Maxillofacial Radiologist interpretation. - $65    ←— *614*
○ No, I will interpret the CBCT/CT volume myself. - $0

CB/CT x-ray preparation for 3D implant planning (Dicom conversion)
If you do not own your own dicom converting software, this step is necessary.
● Please prepare my CBCT x-ray for treatment planning software. - $100
○ No, I am capable of converting Dicom into my own treatment planning software. - $0

Treatment Planning Assistance
Implant Concierge will create an initial treatment plan based on your recommendations and can schedule an online meeting to finalize the treatment plan based on your exact specifications.
● Create initial plan and schedule online meeting to finalize. - $0
○ Create initial plan and deliver case file. - $0
○ I have my own planning software and will not need assistance planning this case. - $0

Computer Generated Surgical Guide
● Process & order a surgical guide for me. - $1000 Max
○ I will not be using a surgical guide for this case. - $0
○ I will order the surgical guide myself. - $0
○ I don't know yet, I will make my decision based on the treatment planning session. - $0

Provisional Restorations
If you ordered a surgical guide through Implant Concierge, provisionals can be fabricated ready at time of surgery
● Yes, fabricate provisionals. - $1000 Max
○ No, I will not order provisionals through the Concierge. - $0

[Next]

*Case Summary*

*Patient Name: Walter N Johnson*
Case ID: 1270840953 — 616a

| CASE PLAN | STATUS | CHARGES |

616b  616c  619 → *Make Changes To This Case Plan*

Current status: Case waiting for dentist to ship diagnostic casts for radiographic template

*Implant Planning Software*
You have chosen the Simplant implant planning system for this case.

*CT/CBCT Scan* ← 618a
The scan will be performed at iMagDent - Austin, Texas. on April 4. at 10:00

*Radiographic Prosthesis*
The Concierge will fabricate a radiographic prosthesis to be used during the CBCT scan process. Endentulous area for radiographic teeth (teeth numbers): 32 31 20 and all maxilla
The finished RP will be shipped to iMagDent - Austin, Texas.

*DICOM Conversion & 3D Preparation*
iMD technicians will convert the format and prepare your DICOM data for use by the Simplant software. A 3D rendered movie will be included.

*Radiology Interpretation*
The Implant Concierge will provide an interpretation of the CBCT volume by a board certified Oral Maxillofacial Radiologist.

*Treatment Planning Assistance*
The Concierge will create an initial treatment plan and schedule an online session to finalize.
Implant brand/type: SureFIT
Type of Prosthetic: maxilla - removable, mandible - fixed
Ideal implant locations (teeth numbers): 1 2 15 16 32 31 17 18

*Computer Generated Surgical Guide*
The Implant Concierge will construct a tooth borne surgical guide for the maxilla arch and a mucosa borne guide for the mandible arch.

*Provisional Restorations*
The Implant Concierge will also provide provisionals.
Type: maxilla - Full Denture With Premium Teeth, mandible - Fixed Acrylic Temporary Screw Retained Refresh Page
Start a New Case
View Current Cases — 621

Dr. Demo
Action Required
When you are ready, click a link below to move to the next step in the case plan.
Click here when diagnostic casts have been shipped ← 620

DENTAL IMPLANT SYSTEM AND METHOD

PRIORITY

This application claims benefit of priority to U.S. Provisional Patent Application Ser. No. 61/332,489, entitled "Dental Implant System and Method" by Bret Royal et al, filed May 7, 2010, which is hereby incorporated by reference in its entirety as though fully and completely set forth herein.

BACKGROUND

1. Field of the Invention

The present invention generally relates to a system and method for providing dental services, and more particularly to a dental implant/surgical guide manufacture and/or planning system and method.

2. Description of Related Art

In providing dental implant treatment, a dentist often makes use of various dental surgical appliances and dental planning software. For example, an implantologist may place an implant in a patient's jaw to secure a replacement tooth. Dentists may fit and place implants, in an effort to replace missing teeth. Unfortunately, the process of providing dental implants accurately may require a series of steps to accurately plan using treatment planning software, order and manufacture surgical guides and accurately place the dental implant(s) and restorative teeth. This can lead to a significant amount of time and effort expended by both, the patient and the dental practitioner. For example, a practitioner may identify a need for a dental appliance/surgical guide for implant therapy at the first patient visit, and may have to schedule a second visit to properly assess the patient's jaw and teeth structure. At the third visit, the patient may have images and/or a mold of the mouth taken. The dental practitioner may then assess the acquired patient data and build a treatment plan. For example, the practitioner may determine which implant treatment options are best suited for the patient's long term oral health. Another patient visit may be scheduled to discuss these options with the patient before moving forward. Then, upon the patient's approval, a request for the dental appliance/surgical guide for implant therapy may then be placed, the dental appliance/surgical guide for implant therapy may then be manufactured, and the dental appliance/surgical guide for implant therapy may finally be installed in a subsequent visit. Often, the dental practitioner may have to oversee coordination between various entities involved in the design and fabrication of the appliance/surgical guide. For example, the dentist may have to coordinate functions between the imaging center, dental laboratories, OMR Radiologists, implant manufactures, and treatment planning and dicom conversion companies, adding complexity to the process. Thus, the process of providing a dental appliance/surgical guide for implant therapy can be time consuming and fragmented for both the patient and the dental practitioner.

Moreover, the process of providing a dental appliance/surgical guide for implant therapy may be complicated by the treatment options available, or the lack thereof. For example, although the dental practitioner may have general expertise, they may not be an expert in a particular aspect of the treatment plan. In some instances, dentists may have to rely solely on their own limited knowledge when preparing a treatment plan, although they would prefer to consult with an expert. Further, while preparing a treatment plan, the dental practitioner may prepare the plan without having any feedback to assess costs associated with certain decisions in implementing the plan. For example, a dental practitioner may have to prepare a complete treatment plan and request a quote from an appliance/implant/service provider to implement the treatment plan, which can take days or weeks. In some instances, the requested plan may be too costly and the dental practitioner may have to modify the treatment plan and request another quote, repeating the process until the treatment plan and the cost are acceptable. Such an iterative process can be time consuming for both the dental practitioner and the patient. A patient may have to wait on the cost estimates before giving approval to move forward. In some instances, even with the initial quite established, the actual costs may exceed the upfront quote or estimate provided to the patient resulting in lost profits or embarrassment to the dental practitioner when they have to explain the situation to the patient.

Moreover, even where an acceptable and cost effective treatment plan is established, manufacture of the dental appliance/surgical guide for implant therapy can be complicated due to number of steps and entities involved. For example, imaging centers, dental laboratories and component manufactures may all have some input to the manufacturing process of said appliances/surgical guides, although they may not have an effective means of communication. For example, they may communicate directly with one another, resulting in decisions that are revealed to some, but not all of the entities involved in the manufacturing process. Further, a lack of communication may slow the manufacturing process and make it difficult for the dental practitioner to establish when the dental appliance/surgical guide for implant therapy will be ready. As a result, the lead time for manufacturing the dental appliance/surgical guide for implant therapy may be increased significantly, and the dental practitioner may be left in the dark, not knowing when the dental appliance/surgical guide for implant therapy will be ready for the patient. This may create scheduling difficulties, as the dental office can not schedule patient's visits that rely on the dental appliance/surgical guide for implant therapy being manufactured and ready for use by the patient.

Accordingly, there is a desire to provide a dental appliance/surgical guide fabrication and planning system and method that provides an efficient manufacturing process and provides feedback to the dental practitioner and all case partners to enable cost effective and efficient dental appliance/surgical guides for implant therapy as well as the ability to complete the process with fewer and more timely patient visits.

SUMMARY

Various embodiments of dental implant treatment plan coordination systems and related apparatus, and methods of operating the same are described. In one embodiment, provided is a method that includes providing a listing of a plurality of user selectable dental implant treatment plan options, wherein the listing is to be displayed on a graphical user interface of a computer system, providing a cost associated with a set of the dental implant treatment plan options selected for inclusion in the dental implant plan, wherein the cost is configured to be displayed in a cost display region of the graphical user interface, receiving, at computer device, an input indicative of a user selection of one or more of the user selectable dental implant treatment plan options for inclusion in the dental implant treatment plan, and providing, in response to receiving the input, an updated cost associated with the with the set of dental implant treatment plan options selected and the user selected one or more dental implant treatment plan options, wherein the updated cost is to be displayed in the cost display region in place of the cost associated with the set of selected dental implant treatment plan options.

In another embodiment, provided is a computer system that includes a dental implant coordinator used to provide a listing of a plurality of user selectable dental implant treatment plan options, wherein the listing is to be displayed on a graphical user interface of the computer system, to provide a cost associated with a set of the dental implant treatment plan options selected for inclusion in the dental implant plan, wherein the cost is to be displayed in a cost display region of the graphical user interface, to receive an input indicative of a user selection of one or more of the user selectable dental implant treatment plan options for inclusion in the dental implant treatment plan, and to provide, in response to receiving the input, an updated cost associated with the with the set of dental implant treatment plan options selected and the user selected one or more dental implant treatment plan options, wherein the updated cost is to be displayed in the cost display region in place of the cost associated with the set of selected dental implant treatment plan options.

In another embodiment, provide is a tangible non-transitory computer readable storage medium having program instructions stored thereon, wherein the computer instructions are executable by a computer to implement a method that includes: providing a listing of a plurality of user selectable dental implant treatment plan options, wherein the listing is to be displayed on a graphical user interface of a computer system, providing a cost associated with a set of the dental implant treatment plan options selected for inclusion in the dental implant plan, wherein the cost is configured to be displayed in a cost display region of the graphical user interface, receiving, at computer device, an input indicative of a user selection of one or more of the user selectable dental implant treatment plan options for inclusion in the dental implant treatment plan, and providing, in response to receiving the input, an updated cost associated with the with the set of dental implant treatment plan options selected and the user selected one or more dental implant treatment plan options, wherein the updated cost is to be displayed in the cost display region in place of the cost associated with the set of selected dental implant treatment plan options.

In another embodiment, provided is a method that includes receiving, at a computer device, a request from a user for at least a portion of dental implant treatment plan application, wherein the dental implant treatment plan application is to be displayed on a graphical user interface of a computer system, retrieving, in response to receiving the request, one or more dental implant treatment plan application preferences associated with the user, and providing the dental implant treatment plan application in accordance with one or more of the preferences associated with the user, wherein the dental implant treatment plan application is to be displayed on a graphical user interface of the computer system.

In another embodiment, provided is a computer system, including a dental implant coordinator used to receive, from a user, a request for at least a portion of dental implant treatment plan application, wherein the dental implant treatment plan application is to be displayed on a graphical user interface of a computer system, to retrieve, in response to receiving the request, one or more dental implant treatment plan application preferences associated with the user, and to provide the dental implant treatment plan application in accordance with one or more of the preferences associated with the user, wherein the dental implant treatment plan application is to be displayed on a graphical user interface of the computer system.

In another embodiment, provide is a tangible non-transitory computer readable storage medium having program instructions stored thereon, wherein the computer instructions are executable by a computer to implement a method that includes: a dental implant coordinator used to receive, from a user, a request for at least a portion of dental implant treatment plan application, wherein the dental implant treatment plan application is to be displayed on a graphical user interface of a computer system, to retrieve, in response to receiving the request, one or more dental implant treatment plan application preferences associated with the user, and to provide the dental implant treatment plan application in accordance with one or more of the preferences associated with the user, wherein the dental implant treatment plan application is to be displayed on a graphical user interface of the computer system.

BRIEF DESCRIPTION OF THE DRAWINGS

Advantages of the present invention will become apparent to those skilled in the art with the benefit of the following detailed description and upon reference to the accompanying drawings in which:

FIGS. 5A-5H are illustrations of exemplary pages displayed by a dentist client application in accordance with one or more embodiments of the present technique.

Figure 1:
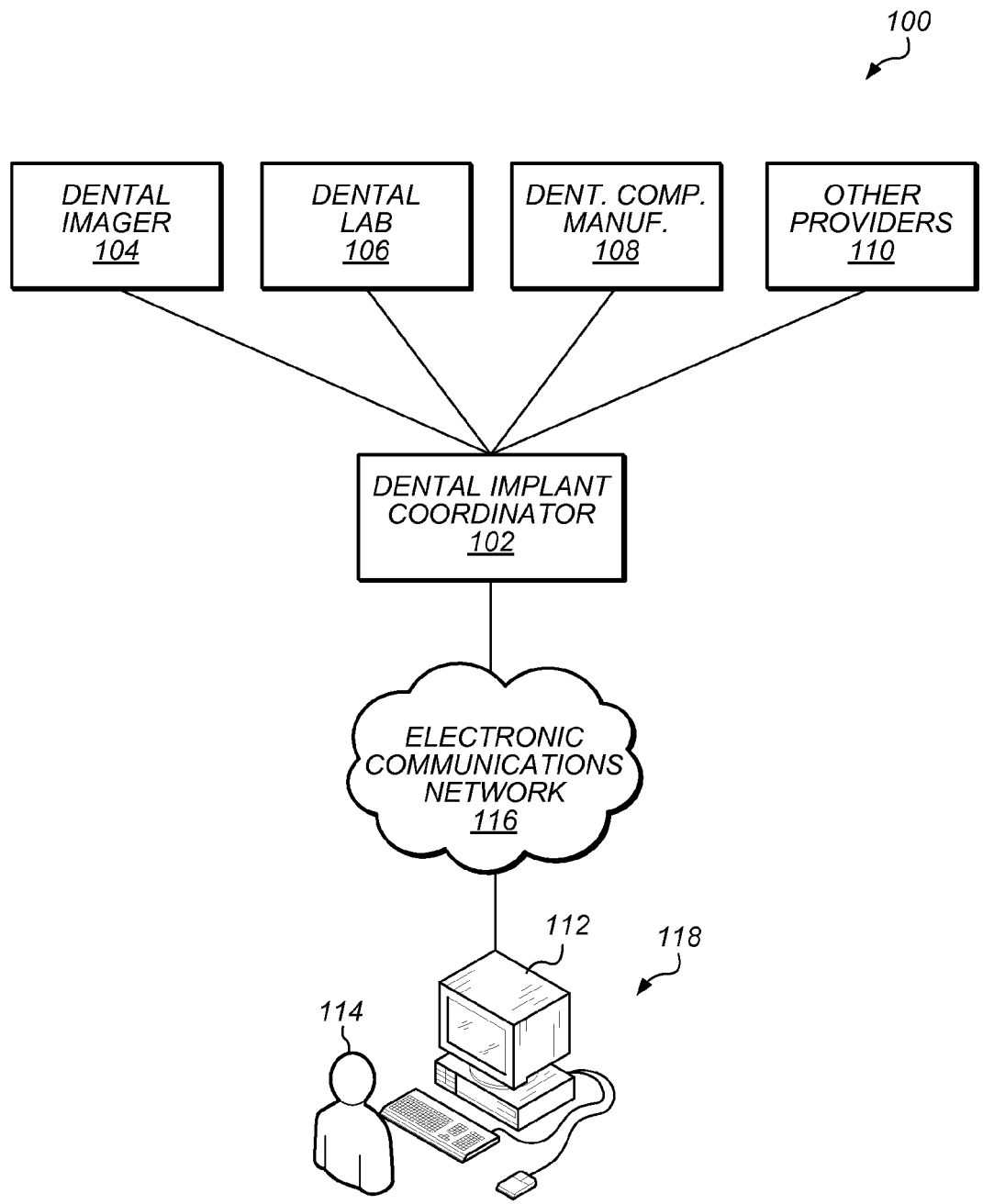
FIG. 1 is a block diagram that illustrates an implant coordination system in accordance with one or more embodiments of the present technique.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF ILLUSTRATIVE EMBODIMENTS

As discussed in more detail below, certain embodiments of the present technique include a dental implant, dental appliance, and/or dental surgical guide for implant therapy manufacture and planning system and method. In some embodiments, a plurality of dental providers/case partners are assembled to provide a treatment plan for dental appliances/surgical guides for implant therapy, such as implant retained dentures. The following disclosure refers extensively to the process of providing implants, although the discussion is not intended to limit the scope of the invention. For example, similar techniques may be provided for all forms of dental implants and appliances. Throughout this document, the term "implant" may be used to refer collectively to one or more of dental implants, dental appliances, dental surgical guides, dental radiographic prosthesis, provisional and/or final restoration dental articles for implant therapy.

Certain embodiments are directed to incorporating all of the processes necessary for dental implants into a centralized provider/coordinator. In some embodiments, a single entity (e.g., coordinator) coordinates, consolidates and effectuates all the processes necessary for guided dental implant therapy, from the initial impression or scan through all steps of the manufacturing and installation process. In certain embodiments, the provider assumes some or all of the responsibility for producing the dental appliances/surgical guides for implant therapy, including vetting and managing associated vendors and pre-negotiated guaranteed pricing and billing.

Certain embodiments are directed to an implant treatment plan that includes a dental practitioner or provider receiving a request for an implant, assimilating dental implant information, providing the implant information to a dental implant coordinator via a web-based interface, the dental implant coordinator generating an implant plan, the dental implant coordinator assigning implant tasks to one or more implant provider entities (e.g., imaging labs, dental labs, component manufacturers) based on the implant plan, design and fabrication of a dental appliance/surgical guide based on the implant plan, and providing the dental appliance/surgical guide to the dental provider for installation and use by the patient.

In some embodiments, receiving the request for the dental appliance/surgical guide and assimilating dental implant information (e.g., information used to fabricate one or more of dental implants, dental appliances, dental surgical guides, dental radiographic prosthesis, provisional and/or final restoration dental articles for implant therapy) includes a doctor of dental surgery (DDS) acquiring an impression of patient's teeth/jaw and/or initial images of patient's teeth/jaw (e.g., radiological template). In certain embodiments, providing the implant information to central implant coordinator includes a DDS providing/uploading impressions/images to the central implant coordinator via a web-interface, using a dental implant application to provide implant treatment plan features (e.g., request mandible/maxilla implant, schedule imaging appointments, select/appoint teeth to be radio opaque, to request radiological interpretations, to request converting a DICOM file to an appropriate format, to request board certified review, additional instructions, etc.). In some embodiments, the application includes a web-based dynamic interface (e.g., a decision tree). In some embodiments, the provider may coordinate exchange of patient information, including CT scans, used for implant treatment planning.

Some embodiments may include a centralized billing technique. In certain embodiments, an implant system includes a repository (e.g., a database) of prices for a myriad of vendors and products including implant manufacturers, dental laboratories, radiologists, imaging facilities, and others. The prices may be pre-negotiated, discounted and/or guaranteed. In some embodiments, during treatment planning/selection, prices are dynamically updated and simultaneously displayed (e.g., on a web page) as choices are made by the prescribing dentist. In certain embodiments, a dynamically updated running-total may be provided such that editing of a treatment plan simultaneously changes the pricing display. Pricing may be guaranteed by the provider (e.g., the entity providing the respective service or product). In some embodiments, the provider acts as a centralized billing and collection agent as it coordinates, consolidates, guarantees, bills and collects for all services for the implant process—one bill to the dentist for the entire process involving multiple vendors.

In some embodiments, the dentist approves or comments on digital images of actual diagnostic wax-ups (the "blue print" for the entire case) and provisional teeth through a secure portal directly with a laboratory, independently or through an interactive real-time web meeting. An entire dental team including a surgeon, the dental laboratory and a restorative dentist may simultaneously and collaboratively generate/review a treatment plan for implants and restoration using an interactive web meeting, CBCT dicom data and treatment planning software. In certain embodiments, the dentists is able to review and comment on portions of the manufacturing process as they occur (e.g., approve a change in design during the manufacturing process).

In some embodiments, a technique is provided to enable secured access to information related to the implant process. In certain embodiments a program may be HIPAA compliant and may parse information according to the accessing party's needs and right to know. For example, in some embodiments, multiple parties involved in the implant process may have selected and/or limited access to certain blocks of information. In some embodiments, a radiologist may have access to clinical information, a laboratory may have to the images and measurements related to surgical guide fabrication or provisional tooth production, and a dentist may have access to all of the information related to the implant process.

In some embodiments, generating an implant plan includes automated scheduling of additional appointments with a patient (e.g., additional impressions, CT scans), generating a case plan sequence, generating cost summary, allowing the DDS to accept/deny/modify implant plan, or providing codes relating to medical reimbursement. In certain embodiments, assigning implant task to one or more implant providers may include assigning task to implant providers based on proximity, providing collaborative reminders for the dental implant process, and/or providing visual indicators of a dental implant status/progress.

Some embodiments may include collaborative reminders/notifications for the dental implant process. In certain embodiments, an implant coordinator may dynamically provide reminder e-mails/messages to implant providers. Reminders may include auto generated notifications based on status points of implant process (e.g., an e-mail to schedule patient follow-up appointments for impressions/scans), auto generated notifications when a step of implant process needs to be completed, auto generated notifications to prompt a DDS, a lab, or a partner to action item for implant process.

Certain embodiments may include visual indications of the dental implant procedure status/progress. In some embodiments, an implant coordinator may dynamically provide indicators to alert a provider that a step needs to be accomplished or provide a dynamically updated "Progress Bar" or "Action Items" for visibly indicating stages of implant treatment process. In certain embodiments, indicators may be provided to a dentist as part of a listing of patients (e.g., all of the DDS's patients). In some embodiments, individual patient data may be accessed via the listing of patients. The display may include a visual indication of task associated with a patient (e.g., green text for complete, red text for first three days old, red-flashing text if the text is more than three days old). In some embodiments, a visual indicator may include a progress bar that provides visual indicator of stages completed, stages not completed (e.g., to be done), and those that are not relevant.

In certain embodiments, a profile and/or preferences may be defined and edited by each dentist. The information may be compiled, stored, and retrieved for the implant process. Preferences may include contact information, a preferred imaging center, preferred implant treatment and planning software, preferred communication options (e.g., e-mail or web notifications) and addresses, preferred agreement terms, preferred billing address, preferred shipping address, and preferred case partners (e.g., adjunct DDS, implant coordinator administrator, dental lab, OMR radiologist, implant representatives, and others). In some embodiments, the dentist may have the option of creating a list of preferences for each interaction with the provider or may use their pre-selected set of clinical directions, e.g., provisional teeth, as well as implant, laboratory, shipping and radiologist preferences. In some embodiments, the preferences are dynamically generated based on prior interactions with the dentist or other dentists having a similar profile to the current dentists.

In some embodiments, a dental implant includes provisional and final restorations, such as dentures. Provisional and final restorations include prosthetic devices constructed to replace missing teeth, and which are supported by surrounding soft and hard tissues of the oral cavity and/or dental implants. Conventional dentures are removable, however there are many different denture designs, some which rely on bonding or clasping onto teeth or dental implants. Removable partial dentures are for patients who are missing some of their teeth on a particular arch. Fixed partial dentures, better known as "crown and bridge", are made from crowns that are fitted on the remaining teeth to act as abutments and pontics made from materials to resemble the missing teeth. Fixed bridges are more expensive than removable appliances but are more stable. Complete dentures or full dentures are worn by patients who are missing all of the teeth in a single arch (i.e., the maxillary (upper) or mandibular (lower) arch).

Turning now to the figures, FIG. 1 is a block diagram that illustrates an implant coordination system 100 in accordance with one or more embodiments of the present technique. In the illustrated embodiment, system 100 includes a dental implant coordinator 102 that is communicatively coupled to other entities of system 100. For example, coordinator 102 may be communicatively coupled to a dental imaging center (imager 104), a dental lab, 106, a dental component manufacturer 108, and other providers 110. Further, coordinator 102 may be coupled to a user computer system 112, as depicted. In some embodiments, computer system 112 is coupled to implant coordinator 102 via an electronic communication network 116, such as the internet. A user 114 may interact with implant coordinator 102 via a computer system 112. In some embodiments, user 114 includes a dental practitioner, such as dentists (e.g., doctor of dental surgery (DDS) or Doctor of Dental Medicine (DDM)), periodontist, and/or their staff, such as a dental or periodontic assistant. For simplicity, user 114 may be simply referred to as a dentist to avoid confusion, although it will be appreciated that a user may include various persons associated with a dental practice, such as those persons working on behalf of the dentist, as described above. Throughout this paper, references to dentists 114 and computer system 112 may referred to collectively as dentist 118. For example, references may be made to dentist 118 sending information to the implant coordinator, although it will be understood that dentist 114 is actually sending information to implant coordinator 102 via computer system 112. Additional descriptions may be provided where necessary to further clarify differentiations between the two.

In the illustrated embodiment, coordinator 102 is depicted as being individually coupled to each of the entities. For example, a direct connection is depicted between dental imaging center 104, lab 106, component manufacturer 108, other providers 110, and dentist 118. In some embodiments, one or more entities of system 100 may be interconnected via the electronic communications network 116. For example, implant coordinator 102, dental imaging center 104, lab 106, component manufacturer 108, other providers 110, and/or computer system 112 may be connected to one another directly or indirectly via network 116. In some embodiments, network 116 may include the internet, a local area network (LAN), a cellular communications network, or the like.

Figure 2:
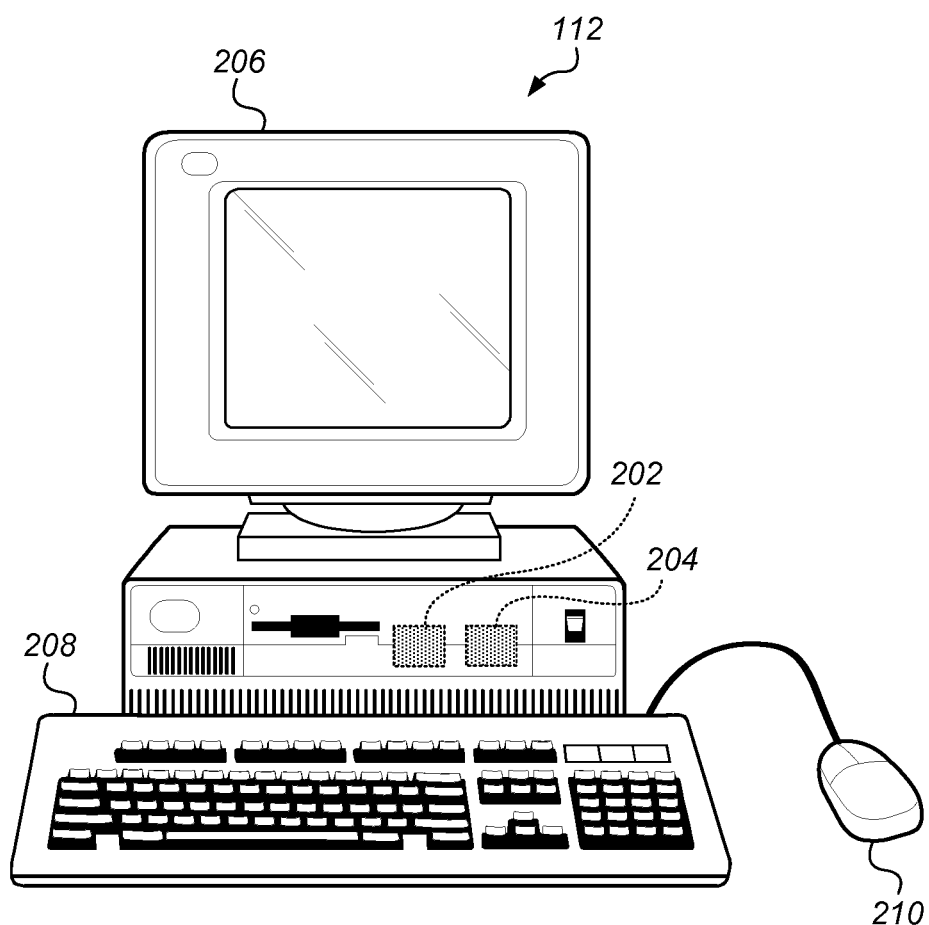
FIG. 2 is a diagram that illustrates computer system in accordance with one or more embodiments of the present technique.

FIG. 2 is a diagram that illustrates computer system 112 in accordance with one or more embodiments of the present invention. Exemplary computer system 112 may be used to implement one or more techniques described herein. In some embodiments, computer system 112 may be operable by a dental practitioner (e.g., dentist 114) or other treatment providers to access and use implant coordinator 102 as described herein. Computer system 112 may include various components such as CPU 202 and a memory medium 204. Memory medium 204 may include a tangible memory medium such as random access memory (RAM), flash memory, hard-drives, and/or CD-ROMs, or the like. Memory medium 204 may include a non-transitory storage medium having program instructions stored thereon that are executable to implement one or more embodiments of the present technique. The program instructions may be executable by CPU 202 to implement one or more methods associated with the preset technique. In the illustrated embodiment, computer system 112 includes a display device 206 (e.g., a monitor), an alphanumeric input device 208 (e.g., a keyboard), and a directional input device 210 (e.g., a mouse). In some embodiments, computer system 112 may include modular and plug-in boards/ cards (e.g., with either commercially available or proprietary hardware) that may be added via a number of expansion slots internal or external to the computer body. Computer system 112 may be connected to a network that enables communication with other computer systems and devices connected to the network. For example, computer system 112 may be connected to the internet and other computer systems (e.g., coordinator 102) via network 116. Computer system 112 may include a wired or wireless connection to network 116 that provides access to the internet. Computer system 112 may access network 116 the internet via a web-browser or similar client application executed thereon. In FIG. 1, computer system 112 is provided for use by dentists 114. It will be appreciated that a similar computer system may be provided at various locations within system 100 or in communication with system 100. In some embodiments, a similar computer system may be provided at implant coordinator 102, dental imaging center 104, lab 106, component manufacturer 108, and/or other providers 110. Such computer systems may be used for executing various routines and enabling access to various components of system 100 as descried above. For example, component manufacturer 108 may implement a similar computer system for receiving orders from implant coordinator 102, processing the orders, and providing the status of orders to implant coordinator 102.

Dental imaging center 104 may include a provider of radiographic images of the patient's mouth. For example, dental imaging center 104 may include a facility (e.g., a dental imaging lab) capable of acquiring dental X-rays, computed tomography (CT) images, or the like. In some embodiments, dental imaging center 104 may be capable of acquiring cone-beam CT ((CB)CT) images.

In some embodiments, system 100 may include a plurality of different dental imaging centers 104 associated with coordinator 102. Each dental imaging center 104 may provide a variety of services (e.g., different imaging techniques) and may have different locations (e.g., dental imaging centers may be located in different parts of a city, state, etc.). As described in more detail below, coordinator 102 may select one of the plurality of dental imaging centers 104 on a case-by-case basis. Coordinator 102 may select an dental imaging center best suited to serve the implant request (e.g., based on types of services needed, location, cost, lead-time, etc.). For example, upon receiving a request for imaging services, coordinator 102 may suggest or select (e.g., assign tasks to) a dental imaging center that provides the needed services and that is in close proximity to the patient or dentist if a lab has not already been specified by the dentist. In some embodiments, a dental imaging center may be selected based on dentist preferences.

In some embodiments, dental imaging center 104 may have a location at or near dentists 118 such that patients can schedule visits with dental imaging center 104 to acquire needed images. For example, dental imaging center 104 may have a physical office location such that a patient can schedule a visit to the office to take the required images. In some embodiments, dental imaging center 104 may provide a mobile imaging unit that is capable of making visits to a location convenient for a patient. For example, dental imaging center 104 may employ a mobile imaging vehicle (e.g., mobile (CB)CT imaging van) that can be provided on-site to patients and dentists 118.

In some embodiments, dental imaging center 104 provides a variety of services related to dental implant procedures. For example, dental imaging center 104 may provide radiologist interpretations, DICOM conversion and 3D preparation, treatment planning assistance, computer generated surgical guides, and the like. In some embodiments, dental imaging center 104 may provide radiological interpretations. For example, dental imaging center 104 may employ a board certified OMR radiologist to provide radiographic interpretations including general pathology and incidental findings of an entire (CB)CT digital volume tomography (DVT).

Dental lab 106 may include one or more dental specialists that provide assistance in making and repairing dental appliances, such as radiographic prosthesis, provisional and/or final dentures, crowns, bridges, and other dental appliances/surgical guides. Dental lab 106 may employ one or more dental technicians who specialize in certain aspects of the dental practice. Dental technicians may seldom work directly with patients, but instead may work with the dentist who makes impressions of the patient's teeth and gums. Dental lab 106 may provide detailed instructions needed to produce dental prosthetics that look good and function well.

In some embodiments, system 100 may include a plurality of different labs 106 and dental imaging centers 104 associated with coordinator 102. Each dental lab 106 and dental imaging centers 104 may provide a variety of services (e.g., different specialties) and may have different locations (e.g., labs may be located in different parts of a city, state, etc.). As described in more detail below, coordinator 102 may select one of the plurality of labs 106/104 on a case-by-case basis. For example, coordinator 102 may select a lab 106/104 best suited to serve the implant request (e.g., based on types of services needed, location, cost, lead-time, etc.). For example, upon receiving a request for lab services, coordinator 102 may suggest or select (e.g., assign tasks to) a lab that provides the needed services and that is in close proximity to the dentist based on pre-determined zip code assignments or geographical proximity if a lab has not already been specified by the dentist. Or, in some embodiments, a lab may be selected based on dentist preferences.

Dental component manufacture 108 may include an entity capable of building the physical dental implant to be provided to the patient. A dental component manufacturer may be able to interpret specification (e.g., images, drawings, and specifications from dental imaging center 104 and/or lab 106) and create a corresponding dental implant (e.g., one or more of dental implants, dental appliances, dental surgical guides, dental radiographic prosthesis, provisional and/or final restoration dental articles for implant therapy). For example, manufacturer 108 may fabricate a dental appliance/surgical guide based on an associated 3D digital model provided by lab 106.

In some embodiments, system 100 may include a plurality of different manufacturers 108 associated with coordinator 102. Each manufacturer 108 may provide a variety of services (e.g., manufacture different types of implants) and may have different locations (e.g., fabricating plants may be located in different parts of a city, state, etc.). As described in more detail below, coordinator 102 may select one of the plurality of manufacturers 108 on a case-by-case basis. For example, coordinator 102 may select a manufacturer best suited to serve the implant request (e.g., based on types of services needed, location, cost, lead-time, etc.) from dentist 118. For example, upon receiving a request for dental implants (e.g., one or more of dental implants, dental appliances, dental surgical guides, dental radiographic prosthesis, provisional and/or final restoration dental articles for implant therapy), coordinator 102 may suggest or select (e.g., assign tasks to) a manufacturer that provides the needed/requested products. In some embodiments, a manufacturer may be selected based on dentist preferences.

Other providers 110 may include one or more other entities relied on by coordinator 102 for effectively planning and implementing the treatment. For example, one provider may include a cost assessment entity that provides coordinator 102 with accurate information regarding pricing for various portions of the implant design and manufacture process. As described in more detail below, in some embodiments, provided cost information may be stored and/or accessed dynamically to provide the dentist with accurate pricing information at the time of filling out a treatment plan application.

In some embodiments, one or more entities of system 100 may be consolidated. For example, one facility may provide some or all of imaging, analysis, and fabrication processes. In some embodiments, some or all of the functions described herein with regard to dental imaging center 104, lab 106, manufacturer 108 and other providers 110 may be provided by implant coordinator 102. For example, coordinator 102 may provide imaging analysis, cost analysis, scheduling, and the like.

Dental implant coordinator 102 may include an entity that consolidates and coordinates various processes of dental implant/dental appliance/surgical guide design and fabrication. In some embodiments, coordinator 102 helps to simplify the implant design and fabrication process by providing a single point of contact for dentists ordering dental implants/dental appliances/surgical guides or provisional restorations, such as dentures, for their patients. Thus, dentist 118 may rely on coordinator 102 to provide various aspects of the dental implant design and fabrication process as opposed to dentist 118 having to individually contact and coordinate various aspects of the implant design and fabrication process (e.g., as opposed to dentist 18 having to directly contact and coordinate processes between dental imaging centers, labs, manufacturers and other providers). As described herein coordinator 102 may facilitate efficient and effective implant design, accurate and readily available pricing information, up-to-date status information regarding the dental implant design and fabrication process, and assistance in scheduling patient care.

As described in more dental below, coordinator 102 may effectuate communication between various entities of system 100 via telephone, mail, e-mail, peer-to-peer computer communication, client/server computer communication (e.g., web-based interfaces), or the like. In some embodiments, coordinator 102 may provide a web-based interface to a dentist to provide a centralized application for providing and receiving information related to all aspects of providing a dental implant.

Figure 3:
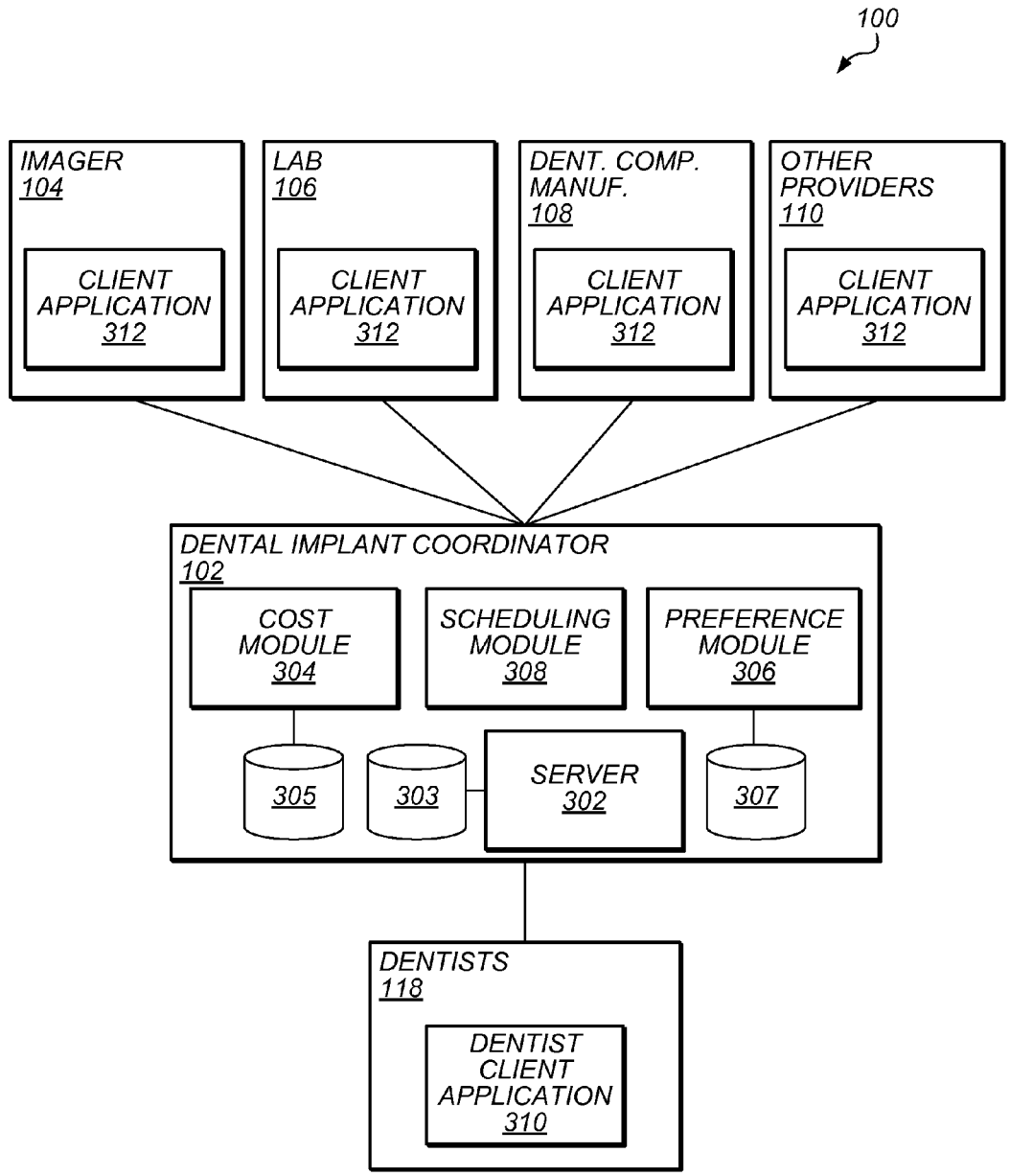
FIG. 3 is a block diagram that illustrates components of the implant coordination system in accordance with one or more embodiments of the present technique.

FIG. 3 is a block diagram that illustrates components of implant coordination system 100 in accordance with one or more embodiments of the present technique. In the illustrated embodiment, coordinator 102 includes a server 302, memory/storage 303, a cost module 304, a cost repository 305, a preference module 306, a preference repository 307, and a scheduling module 308. Dentist 118 includes a dentist client application 310 and each of dental imaging center 104, lab 106, manufacturer 108 and other providers 110 includes a client application 312. Other embodiments may include a variety of different modules, applications, and the like. For example, none or some the entities may include client application 312. Further, portions of coordinator 102 may be consolidated, located remotely and/or provided at other entities of system 100, or not provided at all. For example, memory/storage 303, a cost repository 205, and preference repository 307 may be partially consolidated into one or more storage locations that are located locally or remote to coordinator 102.

In some embodiments, coordinator 102 provides a communication interface for dentist 118 to prepare and monitor various aspects of a dental implant treatment plan. For example, server 302 may include a network-server that communicates with dentist client application 310 running on computer system 112. In some embodiment, dentist client application 310 may include a standalone computer application. For example, dentist client application 310 may include a software package provided by coordinator 102 that is run on computer system 112 to effectuate communication with coordinator 102. In some embodiment, dentist client application 310 may include a web-based application. For example dentist client application 310 may include web-browser run on computer system 112 to effectuate communicate with server 302 of coordinator 102. In some embodiments, server 302 may service a web-page displayed via the dentist client application 310. For example, when dentist 118 logs into dentist client application 310 and begins working on a treatment plan application, a request for a web page may be sent to server 302 from dentist client application 310. Upon receiving the request, server 302 may gather corresponding information from various portions of coordinator 102 and may generate and return a web-page to be rendered at dentist client application 310. For example, server 302 may retrieve a stored web page from memory 303, retrieve/request cost and preference information from cost module 304, cost repository 305, preference module 306, preference repository 307, and/or scheduling module 308, and assemble the information to generate a web-page to be provided to the client application 310. The resulting web-page displayed may provide an interface for providing information from coordinator 102 to dentist 114 and for receiving inputs from dentist 114. For example, where the requested page included a dental treatment plan application, the web-page forwarded form server 302 to dentist client application 310 may provide for the display and entry of patient specific information, such as that described below with respect to dental implant applications. As described in more detail below, in some embodiments, dentist client application 310 may prompt dentist 114 for inputs (e.g., dental implant treatment plan requirements and preferences), and may provide various data (e.g., case plan summaries, status/tasks summaries, cost summaries, patient listings, etc.) relating to one or more dental implant treatment plans. Similar techniques may be applicable to communication with client applications 312 of other entities, such as those of system 100.

Cost module 304 may provide for assessment and determination of cost associated with one or more aspects of a dental implant treatment plans. In some embodiments, cost module 304 may receive an input indicative of one or more dental implant treatment plan options selected by a dentist and may provide an associated cost that can be provided to the dentist. For example, where server 302 receives a page request that may require a response including pricing information, cost module 304 may assess the request and provide an associated cost to be provided. In some embodiments, the cost information may be displayed in association with a treatment plan option, and/or may be used to determine a total cost that is provided to the dentist in response (e.g., a dynamically updated total cost displayed to the user during selection of treatment plan options).

Cost module 304 may include or access a memory store of cost information. For example, cost repository 305 may include cost information associated with one or more dental treatment plan options (e.g., products/processes of an associated dental implant design and fabrication process). In some embodiments, cost repository 304 may store a certain aspect of the dental implant design and fabrication process in association with a corresponding cost. For example, a "radiological interpretation" may be stored in association with its corresponding cost of $65.00. Thus, cost module 304 may provide information including a cost of $65.00 in response to a request for a cost associated with the radiological interpretation. In some embodiments, cost module 304 may assess the stored cost to determine consolidated cost information that may be provided in response to a request. For example, an "iMD DICOM Scan" having a cost of $200, "Radiological interpretation" having a cost of $65.00, "Format DICOM Files for Planning Software" having a cost of $100.00 and "3D Rendered Movie" having a cost of $10.00, may be associated with a total cost of $375.00. Such a consolidation may stream line processing by providing a single cost number when a corresponding group of features/costs are requested. In some embodiments, various groupings may be associated with a cost that is different than the total of the costs for each item of the grouping. For example, a selected grouping of features may be subject to a pricing discount. In some embodiments, cost module 304 may retrieve cost information that is reflective of the discount, and/or may retrieve individual cost and identify and apply any corresponding discounts for the grouping. For example, when all of the above services are requested, the total price for the group may be reduced to $325.00 instead of $375.00, and thus cost module 304 may provide information including a cost of $325 associated with the grouping of services.

In some embodiments, the cost/prices may be pre-negotiated and/or guaranteed prices. For example, pre-negotiated or guaranteed prices provided to coordinator 102 may be stored in cost repository 305. Pre-negotiated and guaranteed prices may include prices that are agreed to by coordinator 102 and other entities of system 100 (e.g., dental imaging center 104, lab 106, manufacturer 108 and other providers 110) such that the cost information stored in cost repository 305 is an accurate reflection of the actual cost and charges for the respective services. Thus, when services are selected by a dentist during design of the treatment plan, the dentists may be provided with an actual cost for the selected services, and not merely an approximation or estimate for the selected services. Accordingly, in some embodiments, module 304 may retrieve pre-negotiated and guaranteed cost information related to selected services from cost repository 304, and may provide accurate pre-negotiated and/or guaranteed prices for delivery to dentists 118 via dentist client application 310 as dentists 114 is making selections (e.g., in real-time), thereby providing dentist 114 an accurate statement of prices to be charged.

In some embodiments, as dentists 118 makes additional selections related to the treatment plan, the pricing information is dynamically updated to reflect the selections. For example, a dentist client application 310 may include a display of a price (e.g., a single number reflective of the total price of all or some of the currently selected treatment options or itemized listing of prices) so that the dentist can track the charges associated with currently selected treatment plan features. The displayed costs/prices may be dynamically updated substantially simultaneous with the making of selections. Thus, a dentists may be provided the cost in real-time as treatment plan selections are made. In some embodiments, as server 302 receives a selection via dentist client application 310 it retrieves associated cost via cost module 304 and cost repository 305, and returns an associated cost to dentist client application 310 for display to dentists 114. For example, if dentist 114 checks a selection box displayed by dentist client application 310 to include a radiologist interpretation at a price of $65, a total cost displayed on dentist client application 310 may be increased by an amount of $65. Conversely, if dentist 114 checks a selection box to remove (e.g., not include) a radiologist interpretation at a price of $65, a total cost displayed by dentist client application 310 may be decreased by an amount of $65. As described in more detail below with respect to FIGS. 5A-5F, in some embodiments, cost information may be displayed simultaneously and in the same browser window with items selected or items to be selected, such that dentists 114 may be able to immediately see associated costs (e.g., a single number reflective of the total price or itemized listing of prices) as treatment plan selections are made. In some embodiments, a total cost may be displayed in another portion of a display of dentist client application 310. For example, a total cost may be displayed in a separate window (e.g., different window of a web-browser) of dentist client application 310 displayed via computer system 112.

In some embodiments, cost information may be provided in association with one or dental treatment plan features displayed. For example, a cost may be displayed in association with a treatment plan feature provided in a dental implant treatment plan. As described in more detail below with respect to FIGS. 5A-5F, in some embodiments, cost information may be displayed proximate a treatment plan option such that a dentist may know the price for using the option prior to making the selection. In some embodiments, itemized pricing information may be provided in a listing/summary of charges, as discussed in more detail below with respect to FIG. 5G. In some embodiments, when server 302 receives a request for a page including cost information, server 302 may retrieve a stored web page from memory 303, retrieve/request cost information from cost module 304 and/or cost repository 305, and assemble the stored web-page information and the cost information to generate a web-page to be provided to the client application 310. For example, the information and layout of dental implant selections may be based on a default set of data having location for the insertion of cost information, and the cost information may be retrieved to provide a web-page having dynamically updated cost/pricing information.

Cost module 304 may facilitate coordinator 102 generating a bill that is provided to the dentist. In some embodiments, upon completing all or some of the dental treatment plan, coordinator 102 may assemble a total cost for charges, and may provide a corresponding invoice to dentist 118. For example, upon completing the dental treatment plan application, upon approving the dental treatment plan, and/or upon completion of the dental implant treatment plan (e.g., after providing the implant to the dentist 118), coordinator 102 may provide an invoice that includes charges associated with the dental treatment plan. In some embodiments, some or all of the charges associated with the dental treatment plan are assimilated into a single bill/invoice. For example, only a single invoice with all of the charges associated with the dental implant treatment plan may be provided to dentist 118, thereby, enabling dentist 118 and/or the patient to provide a single payment for all of the charges associated with the dental implant treatment.

In some embodiments, the charges some or all of the charges may be retrieved via the cost module 304. For example, all of the charges may be based on cost information (e.g., pre-negotiated and guaranteed pricing information) stored in cost repository 305. In some embodiments, charges may be assimilated from sources other than the cost module 304. For example, an entity may separately provide cost information that is assembled with other cost information to enable coordinator 102 to generate a single invoice. Thus, even where an additional charge may be incurred after the total cost is provided in the dental treatment plan application, the dentist may receive a single invoice for all charges, or at least receive multiple invoices from a single entity (e.g., coordinator 102), thereby providing centralized billing from coordinator 102.

Preference module 306 may provide for applying preference to one or more aspects of the dental implant application, design, fabrication, and installation process. In some embodiments, preference module 306 may receive an input indicative of a request to provide certain information relating to a dental implant treatment plan application, design, fabrication, and installation process, and may facilitate providing the information in accordance with pre-determined preferences associated with the request. For example, where server 302 receives a request for information that requires a response, preference module 306 may assess the request and provide response information in accordance with pre-determined preferences associated with the request and/or the requestor. In some embodiments, a dental implant treatment plan may be pre-populated with information based on preferences associated with a requesting user.

In certain embodiments, a profile and/or preferences may be defined and edited by each dentist. For example, dentist 114 may supply one or more preference for the dental implant application, design, fabrication, and installation process via dentist client application 310. Preferences may include contact information, a preferred imaging center, preferred implant treatment and planning software, preferred communication options (e.g., e-mail or web notifications) and addresses, preferred agreement terms, preferred billing address, preferred shipping address, and preferred case partners (e.g., dental imaging center 104, lab 106, manufacture 108, and other providers 110). For example, a dentist preferences may specify a preferred case partner DDS, implant coordinator administrator, dental lab, OMR radiologist, implant representatives, or radiologist. Providing preferred case partners may enable a dentist to easily identify and select certain entities of system 100 without having to search through a listing of potential choices and having to remember which provider they like the best. During the dental treatment plan application process, some of all of the dentist preferences may be automatically selected (e.g., pre-populated), or the dentist may at least be directed to their selection (e.g., the preferred provider may be highlighted, but not selected). In some embodiments, preferences may include pre-selection of certain treatment plan options. For example, where a dentist is located in a given city, delivery may be automatically set (e.g. by default) to a location nearest the city and the dentist 114, or a location previously selected by the dentists. In some embodiments, the dentists most common selections may be automatically selected (e.g. by default). For example, where a dentist has selected a treatment option in three of the last five treatment plans, the option may be pre-selected in future treatment plan applications. In some embodiments, the dentists last selection may be automatically set (e.g. by default). For example, where a dentist has selected a treatment option in the previous treatment plan, the option may be pre-selected in the next treatment plan application. In some embodiments, the dentists identified preferences may be automatically set (e.g. by default). For example, where a dentist has previously indicated their preferences (e.g., via filling out a preferences form), one or more options indicative of the preferences may be pre-selected.

In some embodiments, the dentist may have the option of creating a list of preferences for each interaction with the provider or may use a pre-selected/stored set of preferences. In some embodiments, the preferences are dynamically generated based on prior interactions with the dentist or other dentists having a similar profile to the current dentists. Preference information may be compiled, stored, and retrieved for the implant process. For example, preferences may be processed by preference module 306 and stored in preference repository 307. Preference repository 307 may include a memory location, such as a database, that includes preferences associated with various aspects of providing dental implants.

In some embodiments, preferences are reflected via options displayed to the dentist 114 via dentist client application 310. For example, when dentist 114 logs-into coordinator 102, server 302 may query preference module 306 to retrieve preferences associated with the dentist 114, preference module 306 may retrieve the preferences corresponding to the dentist 118 (e.g., dentist 114, the computer system 112, and/or a specific application 310 used) from preference repository 307 and may provide the corresponding preferences to server 302, and server 302 may assemble and provide a page to be displayed by dentist client application 310 in accordance with the corresponding preferences.

Preferences may be reflected in a display (e.g., a displayed web-page) provided to dentist 114 from coordinator 102, via dentist client application 310. In some embodiments, none, some, substantially all, or all of the available options may be pre-set based on preferences. Such a pre-selection/pre-population based on preferences may enable dentists to quickly complete a treatment plan. For example, a dentist may open a treatment plan, and may have to fill-out only the treatment options that are not pre-selected based on preferences. Moreover, providing default/preferred selections may help to increase accuracy and reduce mistakes. For example, having a default location pre-selected my help to reduce the chance of the dentists accidentally selecting the wrong location.

In some embodiments, implementing preferences may include selecting a particular option. For example, in a web-page provided to and displayed by dentist client application 310, a radio button associated with the option may be pre-selected or a blank for the entry of information may be pre-populated based on the preferences. Dentists may have the option of changing the selection (e.g., unselecting a radio button that was pre-selected in accordance with the preferences). In some embodiments, implementing a preference may include making the preferred option more readily available for selection. For example, where a treatment plan option includes a listing of several possible selections, a preferred selection may be provided at the top of the listing. For example, where the option for a "radiologist interpretation" was listed third, but selected in the last treatment plan filled out by the dentists, the next time the dentists fills-out a treatment plan, the option for a "radiologist interpretation" may be provided as the first option in the list (e.g., at the top of the list). In some embodiments, a selection may be provided with a visual indicator (e.g., having different color text, highlighted, enclosed in a box, provided with an asterisk, etc.) to indicate that it is a preference selection. Such a visual indicator may enable a dentists to navigate directly to the option with minimal effort (e.g., without having to review all of the other options).

Scheduling module 308 may provide for monitoring the status of various tasks associated with the dental implant treatment plan, and/or providing notifications to entities regarding their tasks to complete, task to be completed by other entities, and scheduling. Some embodiments may include scheduling module 308 providing collaborative reminders/notifications for various aspects of the dental implant process. In certain embodiments, an implant coordinator may dynamically provide reminder e-mails/messages to implant providers. Reminders may include auto generated notifications based on status points of implant process (e.g., an e-mail to schedule patient follow-up appointments for impressions/scans), auto generated notifications when a step of implant process needs to be completed, auto generated notifications to prompt a DDS, a lab, or a partner to action item for implant process.

In some embodiments, scheduling module 308 may assign task to one or more entities based on the dental implant treatment plan. For example, upon coordinator 102 receiving a dental implant treatment application, scheduling module 308 may assign the task of "shipping a diagnostic casts for a radio graphic template." Similarly, scheduling module 308 may assign a corresponding task of "receive diagnostic cast for radio graphic template" to coordinator 102 upon receiving notification that the diagnostic cast was shipped by the dentist.

In some embodiments, scheduling module 308 may initiate scheduling of patient appointments to coincide with events related to the dental treatment plan. For example, scheduling module 308 may automatically initiate scheduling a patient for a dentist visit to install the implant when it is determined that the implant is ready for shipping or will soon be ready for shipping to the dentist. Accordingly, scheduling module 308 may facilitate automatic coordination and scheduling of events related to implementing the dental implant application, design, fabrication, and installation process.

In some embodiments, scheduling module 308 may monitor a status of various aspects of dental implant design and fabrication for one or more treatment plans. For example, status monitor may collect and store information from one or more entities (e.g., dental imaging center 104, lab 106, manufacturer 108 and other providers 110) involved in implementing one or more portions of the dental implant treatment plan. In some embodiments, scheduling module 308 may store scheduling information in memory 303 of coordinator 102.

In some embodiments, scheduling monitor 308 may dynamically update and store scheduling information on a regular basis, and/or may provide the current scheduling information upon receiving a request for the scheduling information. For example, status monitor 308 may proactively query other entities for scheduling information (e.g., task status), regardless of whether or not another entity of system 100 has requested scheduling information. In some embodiments, scheduling monitor 308 may receive and/or request scheduling information on a periodic basis (e.g., daily, weekly, etc.). In some embodiments an entity may send scheduling information (e.g., task status) upon occurrence of an event (e.g., a change of status—product entering manufacturing, product ready for shipping, product shipped).

In some embodiments, scheduling module 308 may receive a request for scheduling information from server 302, and may respond with corresponding scheduling information. For example, upon receiving a request to provide case status information from dentist client application 310, server 302 may query scheduling module 308 for scheduling information needed to complete the request (e.g., a summary of a task currently assigned to dentist 118), scheduling module 308 may return the scheduling information to the server 302, and server 302 may assimilate the scheduling information with other information to generate a web-page that is provided to dentist client application 310 for displaying case status.

In some embodiments, scheduling information may be provided in a web-page or similar application. For example, status indicators may be provided when dentist 114 logs-in to dentist client application 310 to review a pending dental implant treatment plan and/or to review a listing of all of their pending treatment plans (e.g., see FIGS. 5E, 5F and 5H). In some embodiments, scheduling information may be provided via e-mail or a similar service. For example, scheduling module 308 may proactively initiate sending of a scheduling/status e-mail to dentist 114 upon a change in status of one or more task associated with the case (e.g., manufacturing complete).

Figure 4:
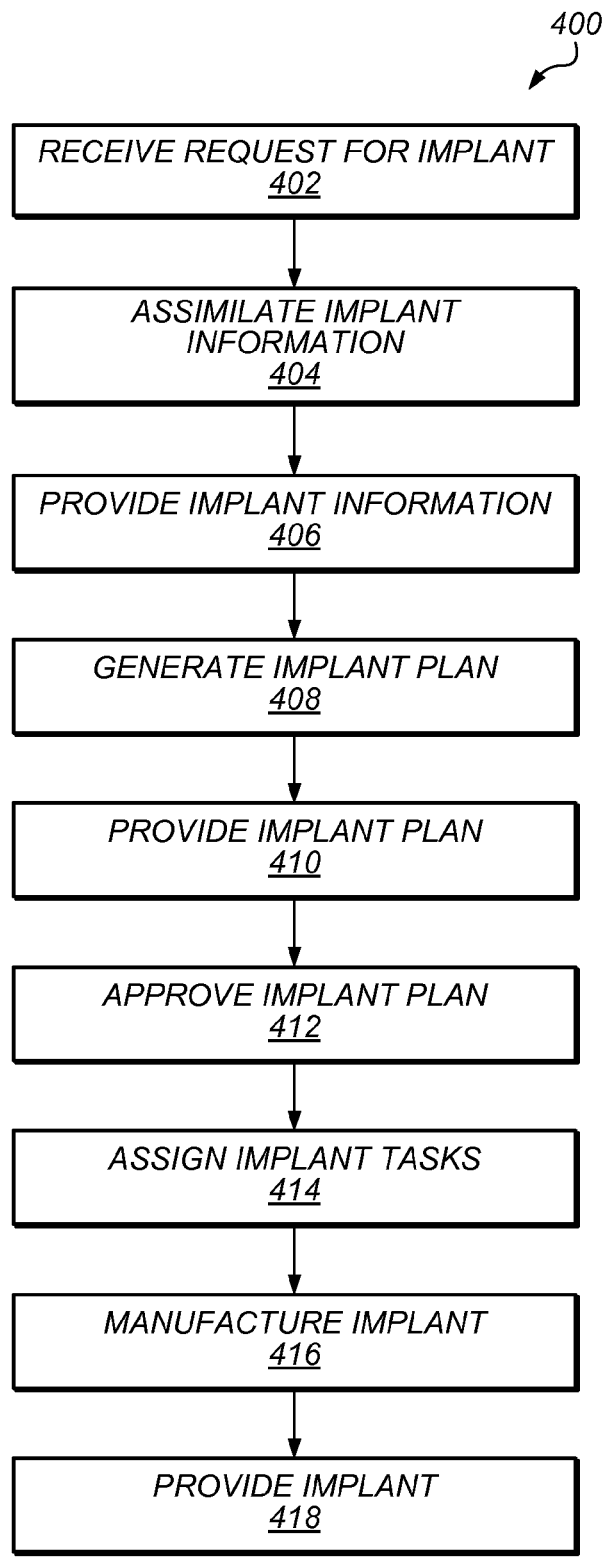
FIG. 4 is a flow chart illustrating a method of providing a dental implant in accordance with embodiments of the present technique.

FIG. 4 is a flowchart that illustrates a method 400 of providing a dental implant in accordance with one or more embodiments of the present technique. Method 400 generally includes receiving a request for an implant, assimilating implant information, providing the implant information, generating an implant plan based on the provided information, providing the implant plan for review, approval of the implant plan, assigning various implant tasks, manufacturing the implant, and providing the implant.

Method 400 includes receiving a request for an implant, as depicted at block 402. In some embodiments, a request for an implant may be initiated by a patient. For example, a patient may visit their dentist with the intention of acquiring dentures. In some embodiments, a dentist may initiate the request for an implant. For example, the patient may visit the dentists without knowing that they need denture, and the dentists may suggests to the patient that they pursue the process of acquiring dentures.

Method 400 may also include assimilating implant information, as depicted at block 404. In some embodiments, assimilating implant information may be done at the time of receiving the request of the implant. For example, a dentists may provide the initial assessment that the patient should pursue the process of acquiring dentures, and may immediately begin to take steps to acquire the appropriate information at that time (e.g., in the same visits). In some embodiments, assimilating implant information may be done at a later time, such as during follow-up visit to the dentist.

In some embodiments, assimilating implant information may include acquiring impressions of a patient's teeth/jaw. For example, a mold may be taken of the patient's mouth. In some embodiments, implant assimilating implant information may include acquiring images of a patient's teeth/jaw. For example, radiological images may include dental X-rays, computed tomography (CT) images, cone-beam CT ((CB)CT) images, or the like. In some embodiments, images may be acquired locally (e.g., at the dentist's office) or remotely, at another location (e.g., an office or mobile location of dental imaging center 104).

Method 400 may include providing implant information, as depicted at block 406. In some embodiments, providing implant information includes providing dental implant information to a coordinator, such as dental implant coordinator 102. In some embodiments, receiving a request for an implant includes coordinator 102 receiving requests for an implant from dentist 118. For example, dentist 114 may initiate filling out a dental implant treatment pan application (e.g., see FIGS. 5A-5C). In some embodiments, dentist 114 may provide information to coordinator 102 via a web-based interface, such as dentist client application 310. The information may be transmitted to coordinator 102 via an electronic network, such as network 116. Thus, dentists 114 may be able to provide dental implant information from the comfort and convenience of a computer system (e.g., computer system 112) located in their own offices. For example, the dental implant information may be uploaded from computer system 112 to coordinator 102 via dentist client application 310 and server 302.

Dental implant information may include the impressions, radiological images, and other information assimilated. In some embodiments, providing dental implant information includes selecting various dental treatment plan options. For example, dentists 114 may access a dental implant treatment plan application via dentist client application 310 running on computer system 112. Displayed interfaces of the dental treatment plan application are discussed in more detail below with respect to FIGS. 5A-5H. The dental implant treatment plan application may provide for the input of patient information (e.g., name, age, sex, etc.). The dental implant application may also provide for selection of a variety of dental implant features and requirements. For example, the dental implant application may enable selection of software to use, selection of arch types (e.g., maxilla, mandible or both), selection of types of radiographic prosthesis (e.g., whether one is required and, if so, who will provide one), selection of X-ray locations (e.g., which facility to have the CT/CBCT X-Ray taken), selection of who is providing a radiological interpretation (e.g., whether or not the coordinator will provide an interpretation of the CB/CT X-ray), selection of image preparation (e.g., converting the image for use with 3D software), any selection of treatment planning assistance (e.g., whether the coordinator or the dentists will complete the treatment plan), selection of whether a surgical guide is needed, selection of whether provisional restorations are needed, selection of radiographic teeth, scheduling of imaging (e.g., when to schedule a CT/CBCT X-ray at a remote location), selections of types of restorations, and for the entry of additional special instructions.

In some embodiments, the interface provides the application in a "decision-tree" format, such that a selection or entry of dental information (e.g., one or more of the selections/answers to the provided questions) dictates some or all of the subsequent requests for selections/information. For example, indicating that a CBCT Scan is to be provided facilitated by the coordinator may cause the dental implant treatment application to follow-up in a second page with a selection regarding when to schedule the scan (e.g., see FIGS. 5B and 5C).

Such a dynamic listing of questions may help to stream line the dental implant application process by eliminating irrelevant questions from the application, thereby enabling dentist 114 to fill out the application quickly and without distractions.

Information regarding selections with the dental implant treatment application may be provided in conjunction with the provided selections. In some embodiments, prices associated with one or more of the selectable features are displayed such that the dentist can assess costs associated with one or more selections (e.g., see FIGS. 5B and 5C). In some embodiments, display of a total running cost is provided. For example, a cost figure is displayed during the application process and the cost figure is dynamically updated as dentist 114 makes various selections. In some embodiments, the cost figure is provided in the same browser/application window as the implant application such that the dentists can view the total cost as selections are made (e.g., see FIGS. 5B and 5C). For example, where a running total cost for selected features is displayed in a window of dentist client application 310, if dentist 114 checks a selection box displayed by dentist client application 310 to include a radiologist interpretation at a price of $65, a total cost displayed on dentist client application 310 may be increased by an amount of $65. Conversely, if dentist 114 checks a selection box to remove (e.g., not include) a radiologist interpretation at a price of $65, a total cost displayed on dentist client application 310 may be decreased by an amount of $65. Cost information may be displayed simultaneously (e.g., in the same browser window) with items selected or items to be selected such that dentists 114 may be able to immediately see associated costs (e.g., a single number reflective of the total price or itemized listing of prices) as dental implant treatment plan selections are made.

In some embodiments, cost information is displayed in association with each selection. For example, a selection for a "radiologist interpretation" that cost $65 may be displayed as "radiological interpretation—$65", such that dentists can assess the cost prior to making the selection (e.g., see FIGS. 5B and 5C). Providing cost information may enable dentist 114 to readily assess the cost of certain implant treatment plan features during the application process. Thus, dentist 114 is not left guessing at the cost for specific features and the total cost until they receive a separate quote for the selected dental treatment plan features. That is, providing prices and a dynamic update of cost information enables the dentist to design a cost effective implant without having to iteratively submit numerous separate application requests and, then, having to identify the best plan.

Use of preferences may be implemented to facilitate simplifying the application process. For example, where preferences are associated with dentist 114 providing dental implant information, default/preferred selections may be provided or suggested. In some embodiments, preferences are reflected via options displayed to the dentist 114 via dentist client application 310. For example, when dentist 114 logs-into coordinator 102, server 302 may retrieve preferences associated with the dentist 114 via preference module 306, and may provide a web-page including those preferences for display at dentist client application 310. In some embodiments, none, some, substantially all, or all of the available options may be pre-set based on preferences. Such a pre-selection based on preferences may enable a dentist to quickly complete a treatment plan. For example, a dentist may open a treatment plan, and may have to fill-out only the treatment options that are not pre-selected based on preferences. Moreover, providing default/preferred selections may help to increase accuracy and reduce mistakes. For example, having a default location pre-selected my help to reduce the chance of the dentists accidentally selecting the wrong location. Further, providing preferred entities may help dentist 114 quickly and easily identity and select an entity to perform a particular portion of the dental implant treatment process.

Method 400 may include generating an implant plan, as depicted at block 408. Generating an implant plan may include assessing the provided implant information and providing a corresponding course of action. In some embodiments, the implant plan is based on the selections made by dentist 114 in the application and/or other information provided (e.g., impressions and images). In some embodiments, coordinator 102 may generate an initial treatment plan based on the application and/or other information provide (e.g., impressions and images) and may provide the initial plan to the dentist for review. For example, an on-line/phone/personal meeting between dentist 114 and a representative of coordinator 102 may be scheduled to discuss the specifics of the initial plan and to finalize the details of the treatment plan moving forward. Online meetings may provide a fast and easy way to work around the dentist's schedule and may provide direct access to expert technicians. In some embodiments, the meeting may include one or more persons of the dentist's dental team such that the dentist and other staff may be apprised of the treatment plan. Dentist 114 may be afforded the opportunity to accept, modify or deny the initial treatment plan. In some embodiments, dentist 114 approves or comments on digital images of actual diagnostic wax-ups (the "blue print" for the entire case) and provisional teeth through a secure portal directly with a laboratory, independently or through an interactive real-time web meeting. An entire dental team including a surgeon, the dental laboratory and a restorative dentist may simultaneously and collaboratively generate/review a treatment plan for implants and restoration using an interactive web meeting, CBCT dicom data and treatment planning software. In certain embodiments, the dentist is able to review and comment on portions of the manufacturing process as they occur (e.g., approve a change in design during the manufacturing process).

Method 400 may include approving the treatment plan, as depicted at block 412. In some embodiments, approving the dental implant treatment plan may include dentist 114 approving of the initial treatment plan. Upon approval of the dental implant treatment plan, coordinator 102 may move forward with implementation of the dental implant treatment plan.

Method 400 may include assigning implant task, as depicted at block 414. In some embodiments, assigning an implant task includes notifying entities (e.g., dental imaging center 104, lab 106, manufacturer 108, other providers 110 and dentist 114) of various tasks that need to be provided. In some embodiments, coordinator 102 may assign tasks based on the final-approved treatment plan. In some embodiments, request may be automated. For example, coordinator 102 may generate a notification/request that is sent to an entity of system 100 designated to complete the task. In some embodiments, each of the entities may provide a response that is indicative of receiving the request, and/or a response that is indicative of confirming or denying the task. Where the task is denied, coordinator 102 may attempt to resolve the conflict with the particular entity, or may attempt to assign the task to another entity capable of fulfilling the task.

In some embodiments, task may include requesting/notifying dental imaging center 104 to provide additional images necessary for implementing the treatment plan. For example, coordinator 102 may send a request for dental imaging center to provide a CT/CBCT Scan at a location selected in the dental treatment plan application. In some embodiments, task may include providing information relating to a custom radiographic prosthesis, radiologist interpretations, DICOM conversion and 3D preparation, treatment planning assistance, computer generated surgical guides, and the like. For example, coordinator 102 may send a request for lab 106 to provide a custom radiographic prosthesis, radiologist interpretations, DICOM conversion and 3D preparation, treatment planning assistance, computer generated surgical guides, and the like. In some embodiments, a task may include requesting lab 106 to forward implant design information (e.g., 3D models) to dental component manufacturer 108 for use in fabricating the dental implant. In some embodiments, task may include requesting/notifying dental component manufacturer 108 to fabricate various components necessary for implementing the treatment plan. For example, once lab 106 has forwarded implant design information (e.g., 3D models) to dental component manufacturer 108 for use in fabricating the dental implant, coordinator 102 may send a request for manufacturer 108 to fabricate the dental implant in accordance with the treatment plan.

Method 400 may include manufacturing the implant (e.g., dental implant, dental appliance, surgical guide, radiographic prosthesis, provisional and/or final restoration) as depicted at block 416. In some embodiments, manufacturing the implant includes one or more of the entities working in cooperation to fabricate the dental implant. For example, dental component manufacturer 108 may fabricate some or all of dental implant in response to tasks generated by implant coordinator 102. Fabrication may be provided in accordance with the treatment plan and information provide from entities of system 100, such as lab 106 and coordinator 102.

Method 400 may include providing the implant, as depicted at block 418. For example, upon completing manufacture of the implant (e.g., dental implant, dental appliance, dental surgical guide, dental radiographic prosthesis, provisional and/or final restoration dental articles for implant therapy), the implant may be sent to the dentist for use. In some embodiments, providing the implant may include completing manufacture of one or both of the actual implant and other components needed for implantation, such as a surgical guide, and providing them to a dentist for implantation in a patient. For example, an implant (and, if needed, a surgical guide) may be provided to a dentist, and the implant may be provided to the patient at a visit to the dentist's office.

In some embodiments, a notification may be provided at various stages of the implant design and fabrication process. For example, where various tasks need to be scheduled coordinator 102 may send out an appropriate notification/request and as various tasks are completed coordinator 102 may be notified. In some embodiments, notifications may be generated and/or received via scheduling module 308 of coordinator 102.

In some embodiments, coordinator 102 may generate and send to one or more entities a notification of one or more tasks that need to be complete. For example, coordinator 102 may send a notification that dental imaging center 104 needs to complete an imaging task, that lab 106 needs to complete and forward an implant design to component manufacturer 108, and/or that dentist 118 needs to ship a diagnostic cast for a radio graphic template. In some embodiments, entities may generate and send status notifications to coordinator 102. For example, dental imaging center 104 may send a notification that a scheduled imaging tasks has been completed, lab 106 may send a notification that an a design has been completed and forwarded to component manufacturer 108, and/or dentist 118 may send a notification that a diagnostic cast has been shipped for a radio graphic template.

In some embodiments, an entity may send a status notification to coordinator upon the occurrence of an event, such as the completion of a scheduled task. For example, dentist 118 may generate a notification upon shipping a cast for a radio graphic template. In some embodiments, an entity may send a status notification to coordinator 102 at a given period of time, such as a periodic (e.g., hourly, daily, weekly, monthly) update. For example, dentist 118 may generate a notification indicative of a current status of shipping a cast, regardless of whether or not there has been a change in status. In some embodiments, notifications may be sent, both, on a periodic basis and upon the occurrence of an event.

In some embodiments, generating a notification may include sending an e-mail to coordinator 102. For example, upon completion of a task or at a given period of time, dentist 118 may generate e-mail that provides coordinator 102 with a status notification. In some embodiments, the e-mail may be generated automatically. For example, automatic notification generation may include computer system 112 generating a notification upon detecting occurrence of an event. In some embodiments, manually generating a notification may include dentist 114 simply entering a notification via dentist client application 310. For example, dentist 114 may simply click on a link or similar entry provided at a web-site to indicate that a given tasks has been completed.

In some embodiments, a notification is provided at or near the time the implant (e.g., dental implant, dental appliance, dental surgical guide, dental radiographic prosthesis, provisional and/or final restoration dental articles for implant therapy) is completed. For example, a notification may be sent from the manufacturer to coordinator 102 a given period of time prior to the completion of manufacture or at the time of manufacture. Such a notification may enable coordinator 102 to inform dentist 118 of an expected delivery date for the implant. In some embodiments, coordinator 102 may schedule and complete various additional tasks based on the completion, or at least expected completion of the implant and/or the expected date of delivery. For example, coordinator 102 may schedule various appointments relating to the installation of the implant. In some embodiments, the scheduling notification may be provided to dentist 118 who, then, schedules related appointments with the patient. For example, dentist 118 may receive the notification that the implant is expected to be delivered on or about a given date, and may contact the patient to schedule an appointment that fits both the dentist's and patient's schedule. In some embodiments, coordinator 102 may send notifications directly to one or both of dentist 118 and the patient. Sending a notification to the patient may relive dentist 118 from having to complete the task of scheduling the appointment and may help to reduce any delay in scheduling the patient appointment that may otherwise occur if dentist 118 were required to handle the task of scheduling the patient appointment as discussed above.

In some embodiments, entities are provided a listing of one or more task assigned to them. For example, dentist 118 may be provided with a listing of patients and various tasks that are associated with one or more of the patients listed. In some embodiments, a dentist is provided with a listing of all of their patients. For example, a listing may include a web-site displayed via dentist client application 310 that displays some or all of dentist's 118 patient having implants designed and manufactured via system 100. In some embodiments, the listing includes an associated visual indicator of status/urgency for tasks associated with each patient. Such visual indicators may enable an entity (e.g., dentist 114) to quickly skim a listing of patients and task to identify what actions they need to take and with what level of urgency. An exemplary patient listing page of, including a listing or patients and corresponding tasks, is discussed below with regard to FIG. 5H.

In some embodiments, a status indicator is provided in association with some or all of the patients in the listing. Status indicators may be indicative of tasks associated with the patient that have been completed and/or tasks associated with the patient that have not been completed (e.g., that need to be completed). In some embodiments, a status indicator includes a visual indication. For example, the status indicator may include a progress bar that visibly indicates the stages of the implant treatment process. The progress bar may be indicative of a percentage of required tasks of the dental implant treatment plan that have been completed. For example, a progress bar that is about 25% filled in may indicate that about ¼ of all of the required tasks of the dental implant treatment plan (e.g., design, fabrication and installation of the implant) have been completed. An exemplary patient listing page including a progress bar, is discussed below with regard to FIG. 5H.

In some embodiments, a progress bar may be indicative of a task that needs to be completed by a given entity. For example, progress bar may take on a given feature to indicate to the viewing entity that they are currently required to complete a task. For example, a progress bar displayed to dentist 114 may turn to a given color (e.g., red) when dentist 114 currently has an outstanding task that they need to complete, and may turn to another color (e.g., green) when dentist 114 currently has no outstanding tasks that need to be completed.

In some embodiments, the progress bar may be indicative of an urgency of a task that needs to be completed by a given entity. For example, progress bar may take on a given feature to indicate to the viewing entity that they are currently required to complete a task that is not due soon, that is due soon or that is overdue. For example, a progress bar displayed to dentist 114 may turn to a given color (e.g., red) when the dentist currently has an outstanding task that has been scheduled for one to three days, and the progress bar may begin to flash in a red color when it has been scheduled for more than three days and has not yet been completed. In some embodiments, the progress bar may turn a different color and/or begin to flash more rapidly to indicate that a due date is approaching or has already passed.

In some embodiments, the listing of patients, task and/or status may be organized by urgency. For example, patients associated with tasks that have been scheduled for a longer period or that are late, may be displayed at the top of the patient listing, where as tasks that are scheduled more recently (e.g., that are relatively new) may be provided toward the bottom of the listing. Thus, the patient/tasks listing may be provided in a descending order of urgency.

Figure 5A:
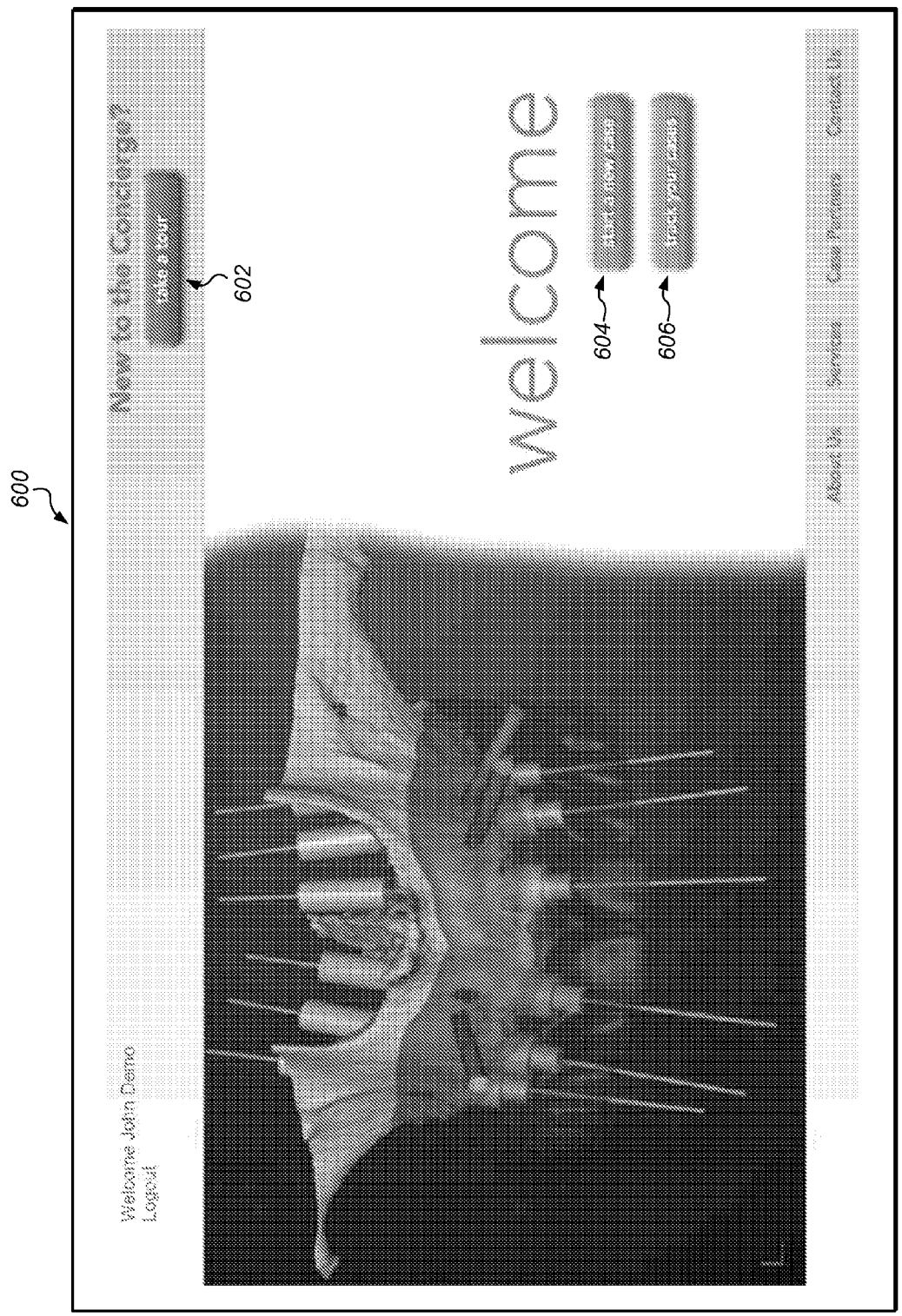

FIGS. 5A-5H are illustrations of exemplary pages that may be displayed by a dentist client application 310 in accordance with one or more embodiments of the present technique. FIG. 5A depicts an exemplary welcome screen of an exemplary browser application. In the illustrated embodiment, the user (e.g., dentist 114) is provided the option to take a tour, start a new case, or track cases via selection of "take a tour" button 602, "start a new case" button 604, or "track your cases" button 606, respectively. Selection of take a tour may enable the user to view options available on the site without having to have or view pending cases. Selection of start a new case may direct the user to one or more application pages that enable the user to fill-out a dental implant treatment plan application, as discussed in more detail below with respect to FIG. 5B-5C. Selection of track your cases may direct the user to one or more application pages that enables the user to view the status of one or more pending dental implant cases, as discussed in more detail below with respect to FIG. 5H. It will be appreciated that the pages maybe interconnected such that user may navigate to each of the pages in a variety of manners.

Figure 5C:
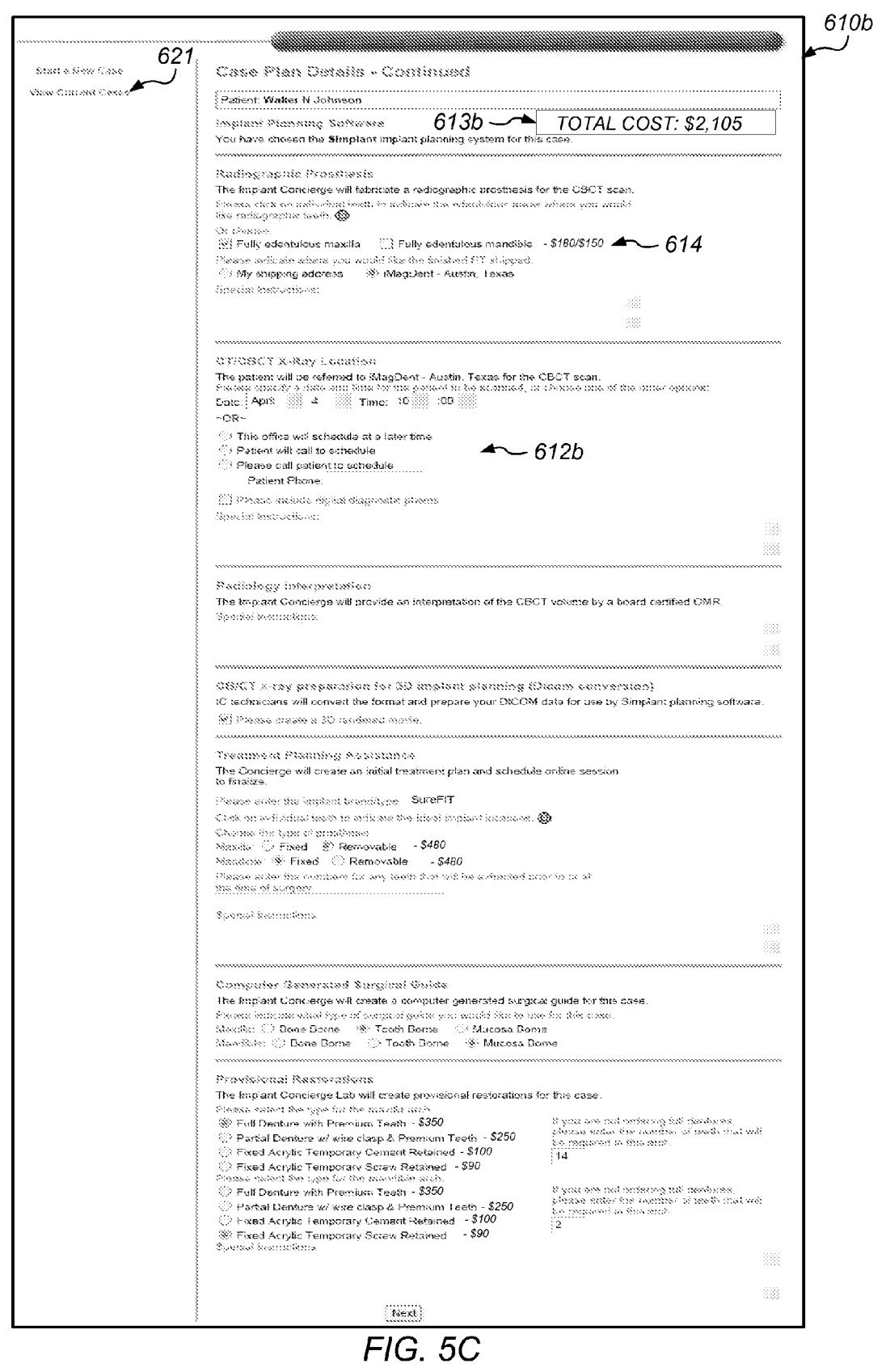

In some embodiments, upon selection by the user to start a new case, dentist client application 310 directs the user to a dental implant treatment plan application. FIGS. 5B and 5C depict exemplary web-page displays of a dental implant treatment plan application 610, in accordance with one or more embodiments of the present technique. In some embodiments, a first page 610*a* may be displayed to enable entry of a first set of implant information, and upon entry and competition of the first set of information, a second page 610*b* may be subsequently displayed to provide for the entry of a second set of implant information. In some embodiments, some or all portions of application 610 (e.g., available selections) may be provided in accordance with dentist preferences. For example, preference module 306 may be consulted in assembly of web-pages to be displayed, as discussed above.

In the illustrated embodiment, first page 610*a* provides for the entry of the first set dental implant information and second page 610*b* provides for the entry of the second set dental implant information. As depicted, in some embodiments, the dental implant treatment plan application may provide for the input of patient information (e.g., name, age, sex, etc.). The dental implant application may also provide for selection of a variety of dental implant features and requirements. For example, the dental implant application may enable selection of software to use, selection of arch types (e.g., maxilla, mandible or both), selection of types of radiographic prosthesis (e.g., whether one is required and, if so, who will provide one), selection of X-ray locations (e.g., which facility to have the CT/CBCT X-Ray taken), selection of who is providing a radiological interpretation (e.g., whether or not the coordinator will provide an interpretation of the CB/CT X-ray), selection of image preparation (e.g., converting the image for use with 3D software), any selection of treatment planning assistance (e.g., whether the coordinator or the dentists will complete the treatment plan), selection of whether a surgical guide is needed, selection of whether provisional restorations are needed, selection of radiographic teeth, scheduling of imaging (e.g., when to schedule a CT/CBCT X-ray at a remote location), selections of types of restorations, and for the entry of additional special instructions.

In some embodiments, the interface provides the application in a "decision-tree" format, such that a selection or entry of information (e.g., one or more of the answers to the provided questions) dictates some or all of the subsequent requests for selections/information. For example, indicating that a CBCT Scan is to be facilitated by the coordinator (e.g., selecting that an iMagDent location will be used for a CBCT scan in a portion 612*a* of page 610*a*) may cause the application to follow-up with a selection (e.g., in second page 610*b*) regarding when to schedule the scan (e.g., portion 612*b* of page 612*b*). Such a dynamic listing of questions may help to stream line the dental implant treatment plan application process by eliminating irrelevant questions from the application process, thereby enabling the dentist to fill out the application quickly and without distractions.

In some embodiments, the second set of questions on second page 610*b* may be generated based on the first set of information provided at first page 610*a*. For example, page 610*a* may include selections/questions relating to a preliminary set of dental implant information and second page 610*b* may be used to provide more detailed selections/questions relevant to the first set of information provided at first page 610a. In some embodiments, some or all selections/questions for display on second page 610b are generated in response to the user selecting the "Next" button, and based on the information provided on first page 610a at that time. Thus, some or all of the selections/questions presented at second page 610b may be dynamically generated based on the first set of information. For example, coordinator 102 may assess the first set of information and provide a second set of selections/question for display in dentist client application 310. In some embodiments, the additional question may be dynamically generated at the time of selection, as opposed to waiting for a user to select the "Next" button. For example, as soon as a user selects an iMagDent location for a CBCT Scan (e.g., portion 612a of first page 610a) a field may be generated (e.g., appear below portion 612a or in a separate window of dentist client application 310) that includes more detailed information relating to the X-Ray location (e.g., similar to that of section 612b of second page 610b). Similar dynamic selection/question generation functionality may be provided for some or all of the selections/questions of application 610.

In some embodiments, cost information is provided in association with and/or based on selections available in the dental implant treatment plan application. In some embodiments, display of a total running cost is provided. For example, in FIGS. 5A and 5B cost figures 613a and 613b are displayed in the upper right hand corner of page 610a and 610b, respectively. Cost figures 613a and 613b may indicate a running total of cost that is based on treatment options currently selected. In some embodiments, the cost figure is dynamically updated as dentist 114 makes various selections in the application. For example, if dentist 114 checks a selection box in the application to include a radiologist interpretation at a price of $65 (see element 614), total cost figure 613a may be increased by an amount of $65. Conversely, if dentist 114 checks a selection box to remove (e.g., not include) a radiologist interpretation at a price of $65, total cost figure 613a may be decreased by an amount of $65. Cost information may be displayed simultaneously (e.g., in the same browser window) with items selected or items to be selected such that dentists 114 may be able to immediately see associated costs (e.g., a single number reflective of the total price or itemized listing of prices) as dental implant treatment plan selections are made. Note, the total cost figure 613b is higher than the total cost figure 612a as it may include both the cost of items previously selected on page 610a and items subsequently selected at page 610b.

In some embodiments, cost information 614 is displayed in association with one or more selection. For example, a selection for a "radiologist interpretation" that cost $65 may be displayed as "radiological interpretation—$65", such that dentists can assess the cost prior to making the selection (e.g., see FIGS. 5B and 5C). Providing cost information 114 may enable dentist 114 to readily assess the cost of certain implant treatment plan features during the application process. Thus, dentist 114 is not left guessing at the cost for specific features and the total cost until they receive a separate quote for the selected dental treatment plan features.

FIG. 5D depicts a case summary page 614 that may displayed to a user via dentist client application 310, in accordance with one or more embodiments of the present technique. In some embodiments, summary page 614 may be displayed upon completion of dental implant application 610. For example, page 614 may be displayed when a user has provided the first and second sets of information provided in response to selections/questions of pages 610a and 610b and selects the "Next" button at the bottom of page 610b.

In some embodiments, case summary page 614 may provide information relating to the current dental treatment plan selections, the status of the case plan, and charges associated with the case plan. For example, in the illustrated embodiments, a user may select the "case plan" tab 616a to view a summary 618a of the case (treatment) plan, as depicted in FIG. 5D. In some embodiments, summary 618a may include the treatment information provided via the dental implant treatment plan application. For example, in the illustrated embodiment, summary 618a provides a concise display of the treatment options selected by the user in the preceding pages (e.g., 610a and 610b). Such a summary may enable the user to quickly review and approve the case plan. If something in summary 618a does not appear to be correct, or if the user would like to edit the case plan, the user may select "Make Changes to This Case Plan" link 619 in the upper right hand portion of page 614.

Figure 5E:
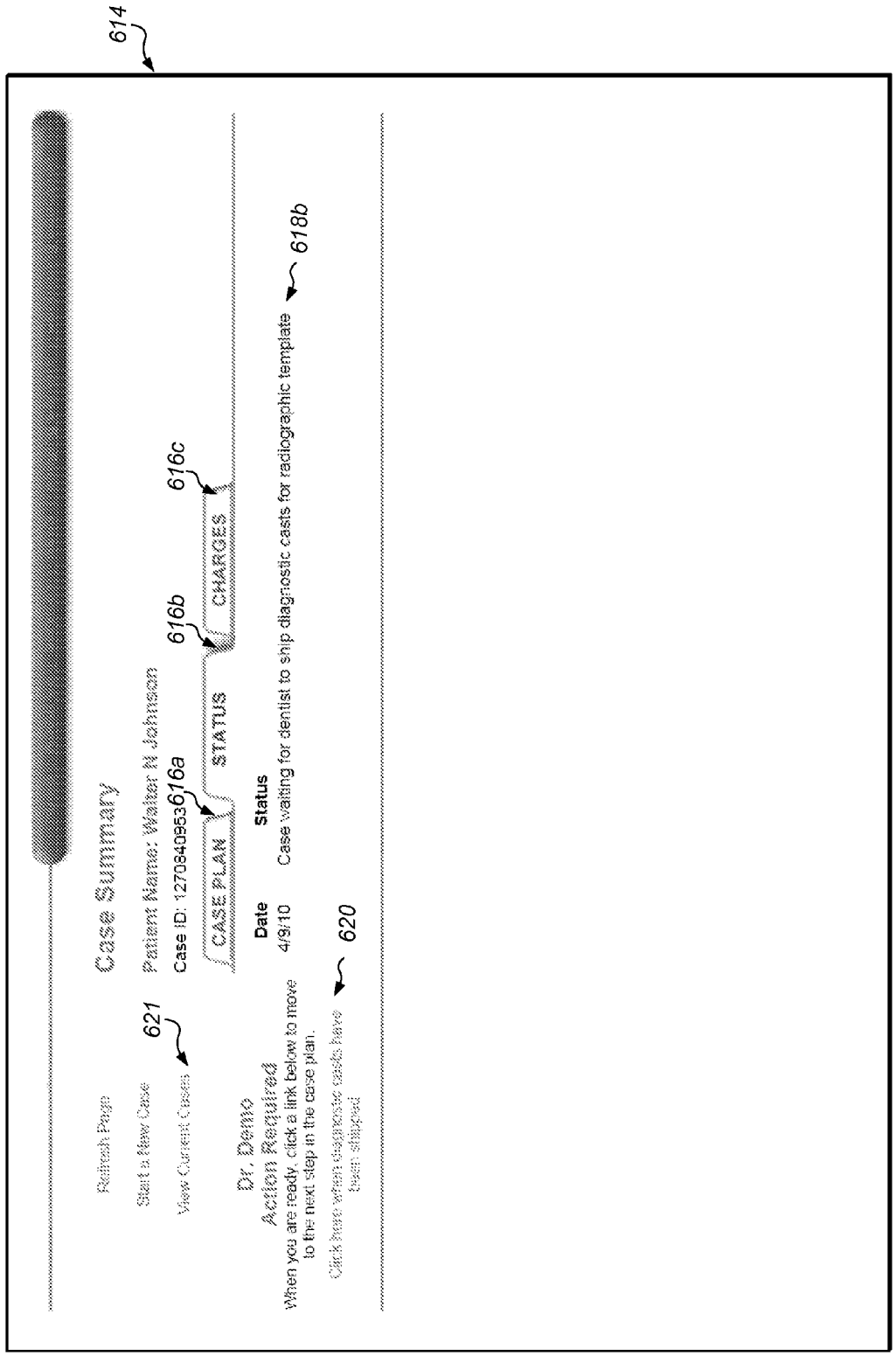
Figure 5F:
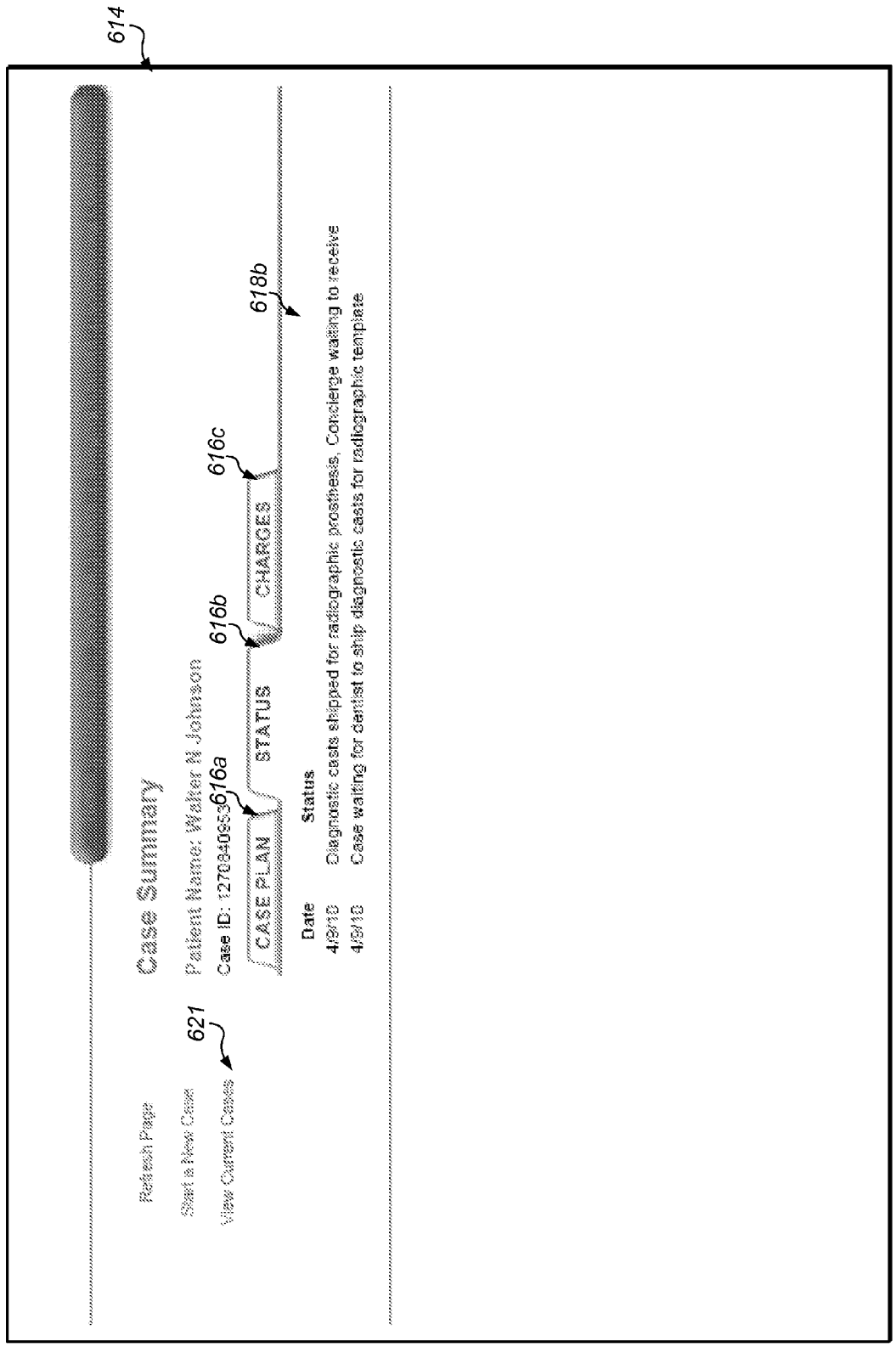

In some embodiments, case summary page 614 may provide information relating to the current status of the case plan. For example, in the illustrated embodiments, a user may select the "status" tab 616b to view a summary 618b of the case status, as depicted in FIG. 5E. In some embodiments, summary 618b includes a listing of the current and/or prior case statuses. For example, in the illustrated embodiment, summary 618b provides a single line indicative of a status of "Case waiting for dentist to ship diagnostic casts for radiographic template" on Apr. 9, 2010. Such a summary may enable the user to quickly review the case to assess what if any action needs to be taken. For example, upon reviewing the summary 618b, dentist 114 may easily identify that they need to ship diagnostic casts for a radiographic template. Thus, the dentist is not left guessing what they should do next, if anything. When the status changes (e.g., when the dentist has shipped the diagnostic casts, dentist 114 may select a "Click here when diagnostic casts have been shipped" link 620 in the left hand portion of page 614. By selecting link 620, dentist 114 may be providing a notification to coordinator 120 (e.g., scheduling module 308) that the associated task has been completed. As discussed above, coordinator 102 may, thus, be apprised of the completion of the task and may send appropriate task to other entities of system 110.

Figure 5G:
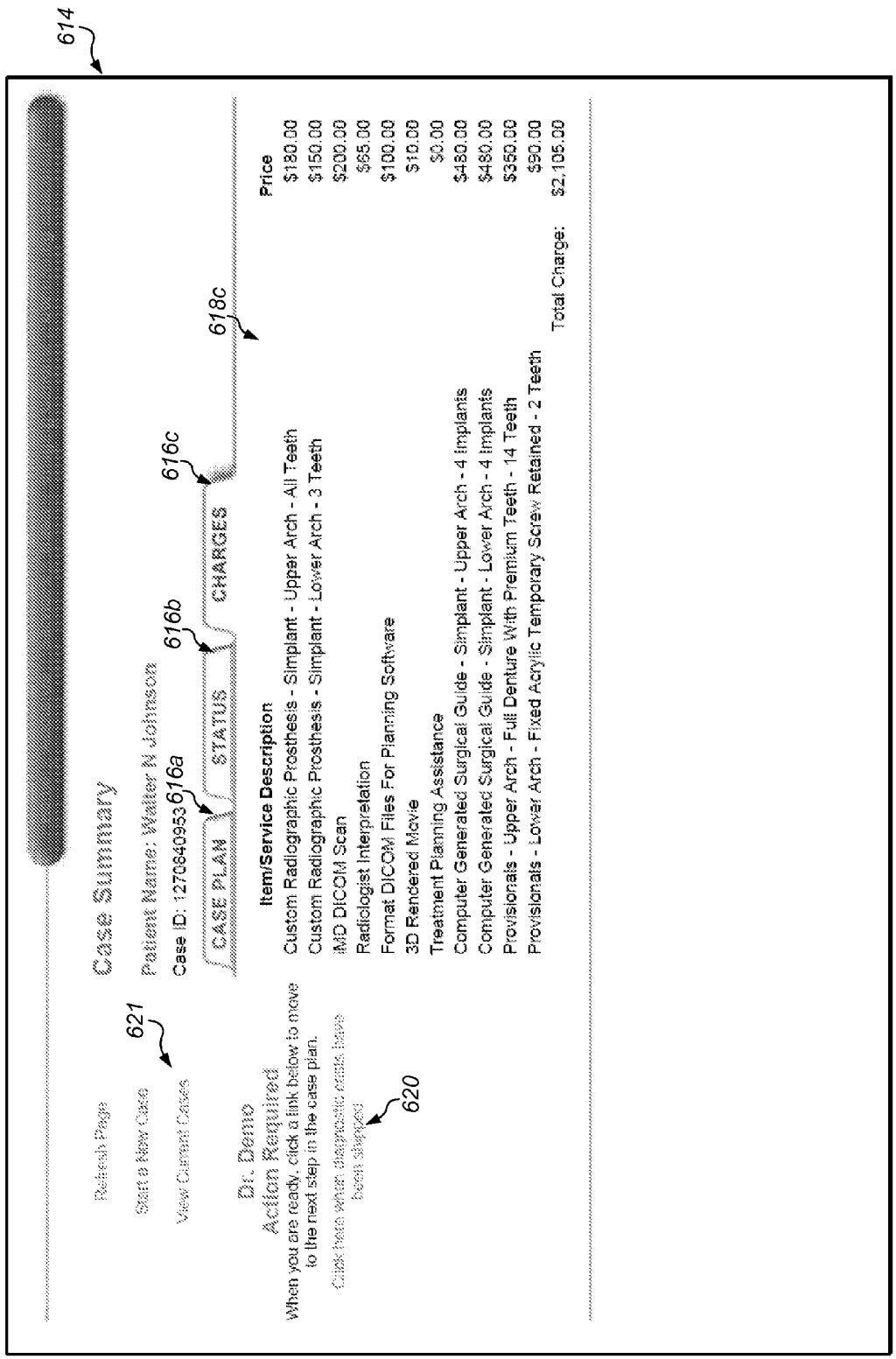
Figure 5H:
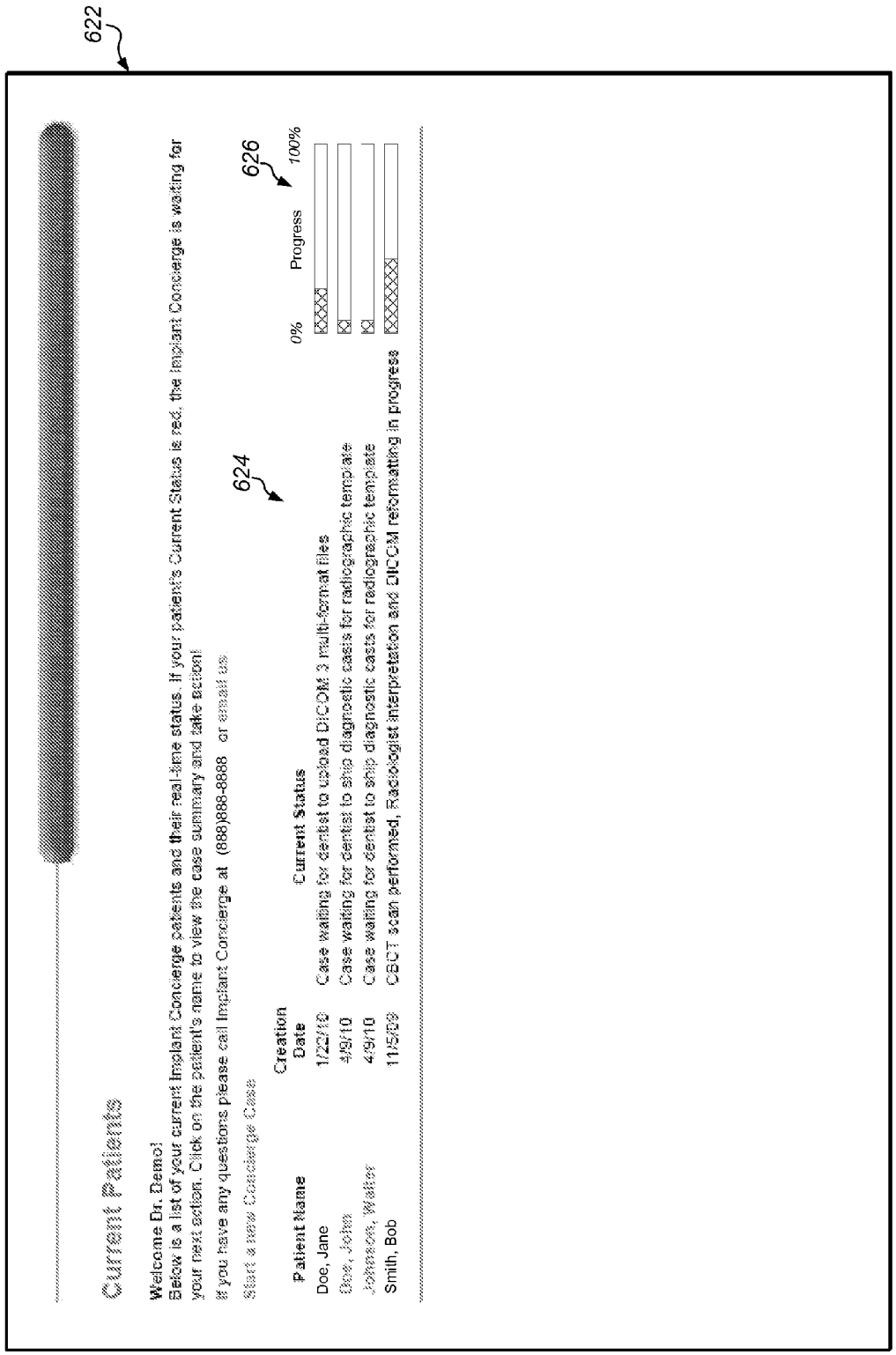

In some embodiments, summary 618b may be dynamically updated to indicate the change in status. For example, as depicted in FIG. 5H, upon providing an indication that "diagnostic casts have been shipped" (e.g., clicking link 620), summary 618b may be updated to show the status of the tasks (e.g., "Diagnostic casts shipped for radiographic prosthesis, Concierge waiting to receive") indicating that the casts have been shipped and another entity (e.g., coordinator 102) is waiting to receive the casts. In some embodiments, a history of the task/status is provided. For example, in the illustrated embodiment, the old status/tasks are provided below the current status. Note, in the illustrated embodiment, the current status does not require any action by the user (e.g., dentist 114) and thus, a link for providing an indicating completion of an associated task (e.g., link 620) is not provided. In some embodiments, multiple tasks may be outstanding, and thus, only links (e.g., links 620) associated with uncompleted/outstanding tasks for dentist 114 are provided and links (e.g., links 620) associated with completed tasks are removed.

In some embodiments, case summary page 614 may provide information relating to the cost/charges associated with the case plan. For example, in the illustrated embodiments, a user may select the "charges" tab 616c to view a summary 618c of the prices/charges associated with the selected treatment plan, as depicted in FIG. 5G. In some embodiments, summary 618c includes an itemized listing of charges for one or more portions of the selected dental implant treatment plan. For example, in the illustrated embodiment, summary 618c provides a listing of "Item/Service Descriptions", each associated with a price. For example, "Radiologist Interpretation" is associated with a price of $65. At a lower right hand corner of the listing, the prices are total to provide a "Total Charge" of $2,105.00. Such a summary may enable the user to quickly review the selected treatment options and their associated cost to afford the user the opportunity to make appropriate changes to the dental implant treatment plan. For example, if upon reviewing the summary 618c, dentist 114 determines that the iMD DICOM Scan is not worth the $200 price, or that a patient can not afford the total charges, dentist 114 may edit the treatment plan options. For example, the user may select "case plan" tab 616a and, then, select "Make Changes to This Case Plan" link 620 in the upper right hand portion of page 614 to make changes to the case plan.

FIG. 5H illustrates a current patient listing page 622, in accordance with one or more embodiments, of the present technique. A user may access the current patient listing by clicking on a "View Current Cases" link 621 in the upper left-hand portion of pages 610a, 610b, and 614. In some embodiments, current patient listing page 622 may include a listing 624 of some or all of patients of dentist 114 (e.g., all of dentist's 114 patient having services provided by coordinator 102). For example, in the illustrated embodiment, listing 624 includes a listing of four of dentist's 114 patients having implant treatment plans being facilitated by system 100. In the illustrated embodiment, listing of patients 624 is arranged alphabetically, although the listing may be arranged based on any variety of criteria. For example, listing 624 may be arranged by creation date of each case, and/or the current status of each case. In some embodiments, cases having tasks to be completed may be provided at the top of the list while cases with no action items (e.g., no tasks to be completed) may be provided at a bottom of the listing 624. For example, in the illustrated embodiment, the first three patients listed are each associated with a case status that is indicative of dentist 114 needing to complete some task (e.g., upload DICOM3 or ship diagnostic casts) for the respective case. In some embodiments, each listing may have a visual feature indicative of the case having one or more tasks that need to be completed and/or an urgency of completing the tasks. For example, in the illustrated embodiment, the status associated with each of the first three patients listed may be provided a first color text (e.g., red) indicative of an outstanding task to be completed and the status associated with the last of the four patients listed may be provided in a second color (e.g., green) indicative of no outstanding task to be completed. In some embodiments, more urgent tasks may be visually indicated. For example, in the illustrated embodiment, the most urgent task may be associated with Jane, Doe, and thus, Jane Doe is listed above patients associated with less urgent task/status. In some embodiments, a visual indicator of urgency may include by providing the text in another color, and/or by providing an animation, such as flashing the text or an associated indicator. Thus, each listing of listing of patients 624 may include visual indicators that vary based on tasks to be completed and/or an urgency associated with each respective task.

In some embodiments, a progress indicator may be provided in association with some or all of the patients listed. For example, in the illustrated embodiment, progress bars 626 are provided in association with each patient of listing 624. Each of progress bars 626 may be indicative of the percent of completion for each of the treatment plans associated with each, respective, one of the patient's listed. For example, in the illustrated embodiment, progress bars 626 indicates that about 25% of the treatment plan associated with Jane Doe has been completed, about 10% of the treatment plans associated with John Doe and Walter Johnson has been completed, and about 40% of the treatment plan associated with Bob Smith has be completed. In some embodiments, progress bars 626 are dynamically updated to reflect changes in status. For example, upon shipping of the cast for Walter Johnson to fulfill the current task, the progress bar may be incremented to a higher percentage, thereby indicating that one additional task of the treatment pan has been completed and that one less task for completing the treatment plan remains outstanding.

In some embodiments, the pages described with respect to FIGS. 5A-5H may include web-pages displayed by dentist client application 310 that are served by server 302 of coordinator 102.

In some embodiments, a technique is provided to enable secured access to information related to the implant process. In certain embodiments, applications running or coordinator (e.g., server 302), dentist client application 310 or client application 312 may be HIPAA compliant and may parse information according to the accessing party's needs and right to know. For example, in some embodiments, multiple parties involved in the implant process may have selected and/or limited access to certain blocks of information. In some embodiments, a radiologist may have access to clinical information, a laboratory may have to the images and measurements related to surgical guide fabrication or provisional tooth production, and a dentist may have access to all of the information related to the implant process.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Furthermore, note that the word "may" is used throughout this application in a permissive sense (i.e., having the potential to, being able to), not a mandatory sense (i.e., must). The term "include", and derivations thereof, mean "including, but not limited to". As used throughout this application, the singular forms "a", "an" and "the" include plural referents unless the content clearly indicates otherwise. Thus, for example, reference to "an implant" includes a combination of two or more implants. The term "coupled" means "directly or indirectly connected".

What is claimed is:

1. A method, comprising:
receiving, at a computer device, an input indicative of a user's geographic location;
providing, on a graphical user interface of the computer device, a listing of one or more providers available for use in planning and implementing a dental implant treatment plan for a patient, wherein the list of available providers is generated based on the user's geographic location;

providing, on the graphical user interface of the computer device, a listing of one or more dental implant treatment and planning software options available for use in planning and implementing the dental implant treatment plan for the patient;

receiving, at the computer device, an input indicative of the user's selection of one of the one or more available dental implant treatment and planning software options;

providing, on the graphical user interface of the computer device, a request for dental implant information for the patient;

receiving, at the computer device, an input indicative of dental implant information for the patient from the user;

providing, on the graphical user interface of the computer device, a listing of a plurality of user selectable dental implant treatment plan options, wherein the listing of the plurality of user selectable dental implant treatment plan options is generated based, at least in part on the user's geographic location, the selected dental implant treatment and planning software option, and the dental implant information for the patient;

providing a cost associated with a set of the user selectable dental implant treatment plan options available for inclusion in the dental implant treatment plan, wherein the cost is configured to be displayed in a cost display region of the graphical user interface;

receiving, at the computer device, an input indicative of a user selection of one or more of the user selectable dental implant treatment plan options available for inclusion in the dental implant treatment plan; and updating the cost displayed in the cost display region of the graphical user interface in response to receiving the input of the user selection of the one or more user selectable dental implant treatment plan options available for inclusion in the dental implant treatment plan.

2. The method of claim 1, further comprising displaying the cost display region of the graphical user interface simultaneously with displaying the listing of user selectable dental implant treatment plan options.

3. The method of claim 1, further comprising displaying the cost display region and the listing of the plurality of user selectable dental implant treatment plan options in one or more web-pages.

4. The method of claim 1, further comprising displaying the cost display region and the listing of the plurality of user selectable dental implant treatment plan options in a display window.

5. The method of claim 1, further comprising displaying the cost display region and the listing of the plurality of user selectable dental implant treatment plan options in different display windows.

6. The method of claim 1, further comprising retrieving cost information from a cost repository of the computer system, wherein the updated cost is based at least in part on the retrieved cost information.

7. The method of claim 6, wherein at least a portion of the cost information comprises pre-negotiated and/or guaranteed pricing information.

8. The method of claim 1, wherein the listing of one or more providers available for use in planning and implementing the dental implant treatment plan for the patient comprises a dental lab, a dental imager, and/or a dental implant manufacturer.

9. The method of claim 1, wherein the dental implant information for the patient comprises information about the patient's teeth obtained from an impression and/or a scan of the patient's teeth.

10. The method of claim 1, wherein the input indicative of dental implant information for the patient from the user comprises visual identification of a status of one or more teeth of the patient by the user.

11. The method of claim 1, wherein the list of available providers is generated based on proximity to the user's geographic location.

12. A system, comprising:
a dental implant coordinator computer system, configured to:
receive, at a computer device, an input indicative of a user's geographic location;
provide on a graphical user interface of the computer device, a listing of one or more providers available for use in planning and implementing a dental implant treatment plan for a patient, wherein the list of available providers is generated based on the user's geographic location;
provide, on the graphical user interface of the computer device, a listing of one or more dental implant treatment and planning software options available for use in planning and implementing the dental implant treatment plan for the patient;
receive, at the computer device, an input indicative of the user's selection of one of the one or more available dental implant treatment and planning software options;
provide, on the graphical user interface of the computer device, a request for dental implant information for the patient;
receive, at the computer device, an input indicative of dental implant information for the patient from the user;
provide, on the graphical user interface of the computer device, a listing of a plurality of user selectable dental implant treatment plan options, wherein the listing of the plurality of user selectable dental implant treatment plan options is generated based, at least in part, on the user's geographic location, the selected dental implant treatment and planning software option, and the dental implant information for the patient;
provide a cost associated with a set of the user selectable dental implant treatment plan options available for inclusion in the dental implant treatment plan, wherein the cost is configured to be displayed in a cost display region of the graphical user interface;
receive, at the computer device, an input indicative of a user selection of one or more of the user selectable dental implant treatment plan options available for inclusion in the dental implant treatment plan; and
update the cost displayed in the cost display region of the graphical user interface in response to receiving the input of the user selection of the one or more user selectable dental implant treatment plan options available for inclusion in the dental implant treatment plan.

13. The system of claim 12, wherein the cost display region of the graphical user interface is configured to be displayed simultaneously with a display of the listing of user selectable dental implant treatment plan options.

14. The system of claim 12, wherein the cost display region and the listing of the plurality of user selectable dental implant treatment plan options are configured to be displayed in one or more web-pages.

15. The system of claim 12, wherein the cost display region and the listing of the plurality of user selectable dental implant treatment plan options are configured to be displayed in a display window.

16. The system of claim 12, wherein the dental implant coordinator computer system comprises a dental implant treatment plan option price repository.

17. The system of claim 16, wherein the dental implant treatment plan option price repository comprises at least some pre-negotiated and/or guaranteed pricing information.

18. The system of claim 17, wherein the updated cost is based at least in part on the pre-negotiated and/or guaranteed pricing information.

19. The system of claim 12, wherein the listing of one or more providers available for use in planning and implementing the dental implant treatment plan for the patient comprises a dental lab, a dental imager, and/or a dental implant manufacturer.

20. The system of claim 12, wherein the dental implant information for the patient comprises information about the patient's teeth obtained from an impression and/or a scan of the patient's teeth.

21. The system of claim 12, wherein the input indicative of dental implant information for the patient from the user comprises visual identification of a status of one or more teeth of the patient by the user.

22. A tangible non-transitory computer readable storage medium having program instructions stored thereon, wherein the computer instructions are executable by a computer system to implement a method, comprising:
   receiving, at a computer device, an input indicative of a user's geographic location;
   providing, on a graphical user interface of the computer device, a listing of one or more providers available for use in planning and implementing a dental implant treatment plan for a patient, wherein the list of available providers is generated based on the user's geographic location;
   providing, on the graphical user interface of the computer device, a listing of one or more dental implant treatment and planning software options available for use in planning and implementing the dental implant treatment plan for the patient;
   receiving, at the computer device, an input indicative of the user's selection of one of the one or more available dental implant treatment and planning software options;
   providing, on the graphical user interface of the computer device, a request for dental implant information for the patient;
   receiving, at the computer device, and input indicative of dental implant information for the patient from the user;
   providing, on the graphical user interface of the computer device, a listing of a plurality of user selectable dental implant treatment plan options, wherein the listing of the plurality of user selectable dental implant treatment plan options is generated based, at least in part, on the user's geographic location, the selected dental implant treatment and planning software option, and the dental implant information for the patient;
   providing a cost associated with a set of the user selectable dental implant treatment plan options available for inclusion in the dental implant treatment plan, wherein the cost is configured to be displayed in a cost display region of the graphical user interface;
   receiving, at the computer device, an input indicative of a user selection of one or more of the user selectable dental implant treatment plan options available for inclusion in the dental implant treatment plan; and
   updating the cost displayed in the cost display region of the graphical user interface in response to receiving the input of the user selection of the one or more user selectable dental implant treatment plan options available for inclusion in the dental implant treatment plan.

23. The computer readable storage medium of claim 22, the method further comprising displaying the cost display region of the graphical user interface simultaneously with displaying the listing of user selectable dental implant treatment options.

24. The computer readable storage medium of claim 22, the method further comprising retrieving cost information from a cost repository of the computer system, wherein the updated cost is based at least in part on the retrieved cost information.

25. A method, comprising:
   receiving, at a computer device, a request from a user for at least a portion of a dental implant treatment plan application, wherein the dental implant treatment plan application is configured to be displayed on a graphical user interface of the computer device;
   retrieving, in response to receiving the request, one or more dental implant treatment plan application preferences associated with the user, wherein the dental implant treatment plan application preferences are retrieved based on a geographic location of the user, the user's selection of a desired dental implant treatment and planning software option from a listing of one or more available dental implant treatment and planning software options, and dental implant information for a patient; and
   providing the dental implant treatment plan application in accordance with one or more of the preferences associated with the user, wherein the dental implant treatment plan application is configured to be displayed on the graphical user interface of the computer device, and wherein the dental implant treatment plan application comprises a listing of one or more dental implant treatment plan options to be selected by the user.

26. A system, comprising:
   a dental implant coordinator computer system, configured to:
   receive, from a user, a request for at least a portion of a dental implant treatment plan application, wherein the dental implant treatment plan application is configured to be displayed on a graphical user interface of the computer system;
   retrieve, in response to receiving the request, one or more dental implant treatment plan application preferences associated with the user, wherein the dental implant treatment plan application preferences are retrieved based on a geographic location of the user, the user's selection of a desired dental implant treatment and planning software option from a listing of one or more available dental implant treatment and planning software options, and dental implant information for a patient; and
   provide the dental implant treatment plan application in accordance with one or more of the preferences associated with the user, wherein the dental implant treatment plan application is configured to be displayed on the graphical user interface of the computer system, and wherein the dental implant treatment plan application comprises a listing of one or more dental implant treatment plan options to be selected by the user.

27. A tangible non-transitory computer readable storage medium having program instructions stored thereon, wherein the computer instructions are executable by a computer system to implement a method, comprising:
   receiving, at a computer device, a request from a user for at least a portion of a dental implant treatment plan application, wherein the dental implant treatment plan application is configured to be displayed on a graphical user interface of the computer device;

retrieving, in response to receiving the request, one or more dental implant treatment plan application preferences associated with the user, wherein the dental implant treatment plan application preferences are retrieved based on a geographic location of the user, the user's selection of a desired dental implant treatment and planning software option from a listing of one or more available dental implant treatment and planning software options, and dental implant information for a patient; and providing the dental implant treatment plan application in accordance with one or more of the preferences associated with the user, wherein the dental implant treatment plan application is configured to be displayed on the graphical user interface of the computer device, and wherein the dental implant treatment plan application comprises a listing of one or more dental implant treatment plan options to be selected by the user.

* * * * *